United States Patent
Cleland et al.

(10) Patent No.: US 7,451,646 B2
(45) Date of Patent: Nov. 18, 2008

(54) DEVICE AND METHOD FOR RESONANT HIGH-SPEED MICROSCOPIC IMPEDANCE PROBE

(75) Inventors: Andrew N. Cleland, Santa Barbara, CA (US); Hyongsok T. Soh, Santa Barbara, CA (US)

(73) Assignee: The Regents of the University of California, Oakland, CA (US)

(*) Notice: Subject to any disclaimer, the term of this patent is extended or adjusted under 35 U.S.C. 154(b) by 205 days.

(21) Appl. No.: 11/460,965

(22) Filed: Jul. 28, 2006

(65) Prior Publication Data

US 2008/0224922 A1   Sep. 18, 2008

Related U.S. Application Data

(60) Provisional application No. 60/703,689, filed on Jul. 28, 2005.

(51) Int. Cl.
*G01N 19/00* (2006.01)
*G01F 23/26* (2006.01)
*A61B 5/05* (2006.01)

(52) U.S. Cl. ............... 73/335.04; 73/304 C; 324/658; 324/686; 340/620; 600/407

(58) Field of Classification Search ........... 73/335.04, 73/304 C; 324/658, 686; 340/620; 600/407
See application file for complete search history.

(56) References Cited

U.S. PATENT DOCUMENTS

| | | | |
|---|---|---|---|
| 2,656,508 A | 1/1953 | Coulter | |
| 4,343,993 A | 8/1982 | Binnig | |
| 4,528,451 A | 7/1985 | Petric | |
| 4,564,436 A | 1/1986 | Buzzonca | |
| 4,676,101 A * | 6/1987 | Baughman | 73/304 C |
| 4,868,396 A | 9/1989 | Lindsay | |
| 4,924,091 A | 5/1990 | Hansma | |
| 4,968,390 A | 11/1990 | Bard | |
| 4,969,978 A | 11/1990 | Tomita | |
| 4,994,818 A | 2/1991 | Keilmann | |
| 5,202,004 A | 4/1993 | Kwak | |
| 5,442,300 A | 8/1995 | Nees | |
| 5,509,300 A | 4/1996 | Chamberlin | |
| 5,519,212 A | 5/1996 | Elings | |
| 5,581,082 A | 12/1996 | Hansma | |
| 5,821,410 A | 10/1998 | Xiang | |
| 5,900,618 A | 5/1999 | Anlage | |
| 5,936,237 A | 8/1999 | van der Weide | |
| 6,351,683 B1 * | 2/2002 | Johnson et al. | 700/121 |
| 6,535,785 B2 * | 3/2003 | Johnson et al. | 700/121 |
| 2005/0043608 A1 * | 2/2005 | Haj-Yousef | 600/407 |

OTHER PUBLICATIONS

T. Leinhos, O. Rudow, M. Stopka, A. Vollkopf & E. Oesterschulze, Coaxial probes for scanning near-field microscopy, Journal of Microscopy, vol. 194, Pt 2/3, May/Jun. 1999, pp. 349-352. Received Dec. 6, 1998; accepted Jan. 30, 1999.

(Continued)

*Primary Examiner*—Nikita Wells
(74) *Attorney, Agent, or Firm*—Quine Intellectual Property Law Group; Stephen J. LeBlanc

(57) ABSTRACT

A resonant high-speed microscopic impedance probe useful for small scale impedance measurements and/or cell and particle counting.

21 Claims, 18 Drawing Sheets

OTHER PUBLICATIONS

Hansma, P.K., Drake, B., et al. (1989) "The scanning ion conductance microscope", Science 243:641-3.

Fee, M., S. Chu, et al. (1989). "Scanning electromagnetic transmission line microscope with sub-wavelength resolution." Optics Communications 69(3-4): 219-24.

Kwak and Bard, Anal. Chem. (1989), 61:1794-1799.

Jiang, G. Q., W. H. Wong, et al. (1993). "Measurement of the microwave dielectric constant for low-loss samples with finite thickness using open-ended coaxial-line probes." and "Open-ended coaxial-line technique for the measurement of the microwave dielectric constant for low-loss solids and liquids." Review of Scientific Instruments 64(6): 1614-26.

Van Der Weide, D. W. (1997). "Localized picosecond resolution with a near-field microwave/scanning-force microscope." Applied Physics Letters 70(6): 677-79.

Van Der Weide, D. W. and P. Neuzil (1996). "The nanoscilloscope: Combined topography and AC field probing with a micromachined tip." Journal of Vacuum Science & Technology B (Microelectronics and Nanometer Structures) 14(6): 4144-7.

Keilmann, F., D. W. van der Weide, et al. (1996). "Extreme sub-wavelength resolution with a scanning radio-frequency transmission microscope." Optics Communications 129(1-2):15-18.

D. R. Schmidt, C. S. Yung, and A. N. Cleland, Phys. Rev. B 69, 140301 (2004).

R. J. Schoelkopf, P. Wahlgren, A. A. Kozhevnikov, P. Delsing, and D. E. Prober, Science 280, 1238 (1998).

D. R. Schmidt, C. S. Yung, and A. N. Cleland, Appl. Phys. Lett. 83, 1002 (2003).

* cited by examiner (a) Cantilever with integrated probe (ground on top with apertures, signal underneath with isolating layer between, with windows in ground plane)

(b) Operated as AFM in inverted geometry with laser for AFM-style deflection detection and rf probe for sensing local impedance.

(a) Deposit signal electrodes  (b) Deposit insulator  (c) Deposit ground plane

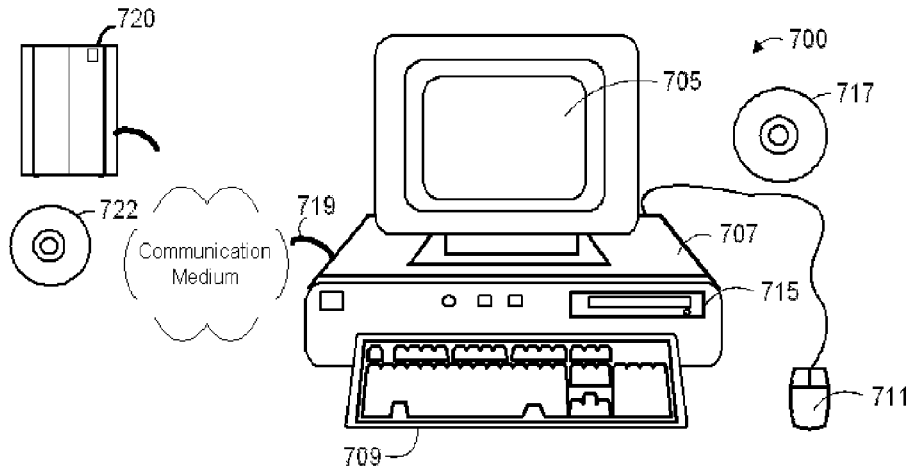

FIGURE 25

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

FIGURE 26 (TABLE 1)

DEVICE AND METHOD FOR RESONANT HIGH-SPEED MICROSCOPIC IMPEDANCE PROBE

CROSS REFERENCE TO RELATED APPLICATIONS

This application claims priority from provisional patent application 60/703,689 filed 28 Jul. 2005 and incorporated herein by reference.

Portions of this Invention were made with government support under Grant (Contract) No. DAAD19-03-D-0004 awarded by the Department of Defense. The Government has certain rights to this invention.

Portions of this Invention were made with government support by the DMEA/DARPA Center for Nanoscience Innovation for Defense, and the ONR Young Investigator Program N000140410456. The Government has certain rights to this invention.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

BACKGROUND US PATENTS

| Patent No. | Date | Description | Class |
|---|---|---|---|
| 4528451 | July 1985 | Petric et al. "Gap control system for localized vacuum processing" | 250/441. |
| 4564436 | January 1986 | Buzzonco et al. "Apparatus for measuring the degree of sensitization of metal articles" | 204/400. |
| 4868396 | September 1989 | Lindsay, "Cell and substrate for electrochemical STM studies" | 250/440. |
| 4924091 | May 1990 | Hansma et al., "Scanning ion conductance microscope" | 250/306. |
| 4968390 | November 1990 | Bard et al., "High resolution deposition and etching in polymer films" | 204/15. |
| 4969978 | November 1990 | Tomita et al., "Apparatus and method for tunnel current measurement observed simultaneously with electrochemical measurement" | 204/153. |
| 4343993 | August 1982 | Binnig et al., "Scanning tunneling microscope" | 350/306. |
| 4994818 | February 1991 | Keilmann, "Scanning tip for optical radiation" | |
| 5202004 | April 1993 | Kwak et al., "Scanning electrochemical microscopy" | 205/790.5 |
| 5442300 | August 1995 | Nees et al., "Ultrafast electrical scanning force microscope probe" | |
| 5900618 | May 1999 | Anlage et al., "Near-field scanning microwave microscope having a transmission line with an open end" | 250/201.3 |
| 5509300 | April 1996 | Chamberlin et al., "Non-contact force microscope having a coaxial cantilever-tip configuration" | 73/105. |
| 5519212 | May 1996 | Elings et al., "Tapping atomic force microscope with phase or frequency detection" | 250/234. |
| 5581082 | December 1996 | Hansma et al., "Combined scanning probe and scanning energy microscope" | |
| 5936237 | August 1999 | van der Weide, "Combined topography and electromagnetic field scanning probe microscope" | 250/234. |
| 5821410 | October 1998 | Xiang et al, "Scanning tip microwave near field microscope" | 73/105 |

OTHER PUBLICATIONS

Ash, E. A., et al., "Super-Resolution Aperture Scanning Microscope", Nature, vol. 237, Jun. 30, 1972, pp. 510-512.

Bard et al., Anal. Chem., (1989), 61: 132.

Blanc, N., J. Brugger, et al. (1996). "Scanning force microscopy in the dynamic mode using microfabricated capacitive sensors." Journal of Vacuum Science & Technology B (Microelectronics and Nanometer Structures) 14(2): 901-5.

Bryant, C. A., et al., "Noncontact Technique for the Local Measurement of Semiconductor Resistivity", The Review of Scientific Instruments, vol. 36, No. 11, November, 1965, pp. 1614-1617.

Chevalier, B., M. Chatard-Moulin, et al. (1992). "High temperature complex permittivity measurements of composite materials using an open-ended waveguide." Journal of Electromagnetic Waves and Applications 6(9): 1259-75.

Danzebrink, H. U., G. Wilkening, et al. (1995). "Near-field optoelectronic detector probes based on standard scanning force cantilevers." Applied Physics Letters 67(14): 1981-3.

Durig, U., D. Pohl, et al. (1986). "Near-field optical scanning microscopy with tunnel-distance regulation." IBM J. Res. Develop. 30(5): 478-83.

Fee, M., S. Chu, et al. (1989). "Scanning electromagnetic transmission line microscope with sub-wavelength resolution." Optics Communications 69(3-4): 219-24.

Golosovsky, M., A. Galkin, et al. (1996). "High-spatial resolution resistivity mapping of large-area YBCO films by a near-field milimeter-wave microscope." IEEE Transactions on Microwave Theory and Techniques 44(7, pt.2): 1390-2.

Gutmann, Ronald J., et al., "Microwave Scanning Microscopy for Planar Structure Diagnostics", IEEE MTT-S Digest, 1987, pp. 281-284.

Hansma, P. K., Drake, B., et al. (1989) "The scanning ion conductance microscope", Science 243: 641-3.

Indermuhle, P.-F., G. Schurmann, et al. (1997). "Self-sharpening tip integrated on micro cantilevers with self-exciting piezoelectric sensor for parallel atomic force microscopy." Applied Physics Letters 70(17): 2318-20.

Jiang, G. Q., W. H. Wong, et al. (1993). "Measurement of the microwave dielectric constant for low-loss samples with finite thickness using open-ended coaxial-line probes." Review of Scientific Instruments 64(6): 1622-6.

Jiang, G. Q., W. H. Wong, et al. (1993). "Open-ended coaxial-line technique for the measurement of the microwave dielectric constant for low-loss solids and liquids." Review of Scientific Instruments 64(6): 1614-21.

Keilmann, F., D. W. van der Weide, et al. (1996). "Extreme sub-wavelength resolution with a scanning radio-frequency transmission microscope." Optics Communications 129(1-2): 15-18.

Kwak and Bard, Anal. Chem. (1989), 61: 1794-1799.

Lieberman, K., A. Lewis, et al. (1994). "Multifunctional, micropipette based force cantilevers for scanned probe microscopy." Applied Physics Letters 65(5): 648-50.

Mihalcea, C., A. W. Scholz, et al. (1996). "Multipurpose sensor tips for scanning near-field microscopy." Applied Physics Letters 68(25): 3531-3.

Misra, D., M. Chabbra, et al. (1990). "Noninvasive electrical characterization of materials at microwave frequencies using an open-ended coaxial line: test of an improved calibration technique." IEEE Transactions on Microwave Theory and Techniques 38(1): 8-14.

Noell, W., M. Abraham, et al. (1997). "Micromachined aperture probe tip for multifunctional scanning probe microscopy." Applied Physics Letters 70(10): 1236-38.

Osofsky, S. S. and S. E. Schwarz (1992). "Design and performance of a noncontacting probe for measurements on high-frequency planar circuits." IEEE Transactions on Microwave Theory and Techniques 40(8): 1701-8.

Rugar, D. and P. Hansma (1990). "Atomic force microscopy." Physics Today (Oct.): 23-30.

Ruiter, A. G. T., M. H. P. Moers, et al. (1996). "Microfabrication of near-field optical probes." Journal of Vacuum Science & Technology B (Microelectronics and Nanometer Structures) 14(2): 597-601.

Soohoo, R. F., "A Microwave Magnetic Microscope", Journal of Applied Physics, vol. 33, No. 3, March 1962, pp. 1276-1277.

Synge, E. H., "A Suggested Method for Extending Microscopic Resolution into the Ultra-Microscopic Region", Philos. Mag., vol. 6, 1928, pp. 356-362.

Tortonese, M., R. C. Barret, et al. (1993). Applied Physics Letters 62: 834-36.

Van Der Weide, D. W. (1997). "Localized picosecond resolution with a near-field microwave/scanning-force microscope." Applied Physics Letters 70(6): 677-79.

Van Der Weide, D. W. and P. Neuzil (1996). "The nanoscilloscope: Combined topography and AC field probing with a micromachined tip." Journal of Vacuum Science & Technology B (Microelectronics and Nanometer Structures) 14(6): 4144-7.

Vlahacos, C. P., R. C. Black, et al. (1996). "Near-field scanning microwave microscope with 100 mu m resolution." Applied Physics Letters 69(21): 3272-4.

Wei, T., X. D. Xiang, et al. (1996). "Scanning tip microwave near-field microscope." Applied Physics Letters 68(24): 3506-8.

Xu, Y., F. M. Ghannouchi, et al. (1992). "Theoretical and experimental study of measurement of microwave permittivity using open ended elliptical coaxial probes." IEEE Transactions on Microwave Theory and Techniques 40(1): 143-50.

REFERENCES REGARDING FLOW CYTOMETRY

S. Gawad, L. Schild, P. Renaud, "Micromachines impedance spectroscopy flow cytometer for cell analysis and particle sizing", *Lab on a Chip* 1, 76-82 (2001).

S. Gawad, K. Cheung, U. Seger, A. Bertsch, P. Renaud, "Dielectric spectroscopy in a micromachined flow cytometer", *Lab on a Chip* 4, 241-251 (2004).

L. L. Sohn, O. A. Saleh, G. R. Facer, A. J. Beavis, R. S. Allan, D. A. Notterman, "Capacitance cytometry: Measuring biological cells one by one", *Proc. Natl. Acad. Sci.* 97, 10687-10690 (2000).

G. R. Facer, D. A. Notterman, L. L. Sohn, "Dielectric spectroscopy for bioanalysis: From 40 Hz to 26.5 GHz in a microfabricated wave guide", *Appl. Phys. Lett.* 78, 996-998 (2001)

REFERENCES REGARDING COULTER COUNTERS

W. H. Coulter, U.S. Pat. No. 2,656,508: Means for counting particles suspended in a fluid, 1953.

A. G. Tibbe et al., Cytometry 47, 163 (2002).

M. Berger, J. Castelino, R. Huang, M. Shah, and R. H. Austin, Electrophoresis 22, 38833892 (2001).

M. Durr, J. Kentsch, T. Muller, T. Schnelle, and M. Stelzle, Electrophoresis 24, 722 (2003).

M. M. Wang et al., Nat. Biotechnol. 23, 83 (2005).

SUMMARY

The present invention, in specific embodiments, involves novel devices and/or methods for performing electronic measurements in very small-scale volumes, e.g., less then about 1 cubic millimeter. In further embodiments, the invention provides a device and/or method for conducting such measurements using high electromagnetic frequencies, allowing for greater resolution and faster measurement times. In further embodiments, the invention involves novel and improved methods for counting small particles such as beads or cells at high speed using electronic measurements.

In specific embodiments, the invention provides methods for the fabrication of devices and/or systems in accordance with the invention.

According to specific embodiments, the invention involves a radiofrequency, inductively-coupled probe that comprises a conducting probe electrode, a conducting grounded shield, and a detecting end of the probe electrode which can be constructed as a small aperture in the shield electrode or by other separation from the shield electrode. The probe electrode is connected through a radiofrequency inductor to measurement and/or stimulation electronics. The detecting end of the probe can be based on either a coaxial or a planar (thin film) or other geometries.

A probe according to specific embodiments of the invention can make quantitative measurements of the electrical impedance of samples placed in close proximity to the detecting end of the probe. Samples can include metals, semiconductors, insulators, as well as electrolytic fluids, and fluids with distinct solid or liquid or semi-solid particles. Impedance can be measured from low to microwave frequencies when a sample is placed in close proximity to the detecting end of the probe. In various example embodiments and implementations, measurement frequencies can range from $10^0$-$10^{10}$ Hz or higher; the sample impedance can range from $10^1$ to $10^9$ ohms; and time-domain impedance measurements can be made with a time resolution on the order of $10^{-9}$ seconds. Measurements are made by exciting the probe with electrical signals at one or more excitation frequencies f, and monitoring the fraction of the radiofrequency power reflected from the probe, a quantity termed the reflectance and denoted by "$S_1$", and monitoring any combination of the absolute reflectance $Abs[S_1]$, the real part of the reflectance $Re[S_1]$, or the imaginary part $Im[S_1]$, as a function of excitation frequency f and time t. Another term commonly used is the reflection loss Γ, defined by $Γ=1-Abs[S_1]$.

In electrolytic applications, the probe can be further sensitized through the addition of surface coatings of organic or inorganic compounds. The probe can operate either as a static sensor, yielding dynamic impedance values at a single physical location, or can be operated as a scanned instrument, so that one-, two- or three-dimensional impedance images with spatial resolution from, e.g., 1 nm to 1 mm can be generated, as a function of excitation frequency f and time t. The probe can also be combined with a scanned probe of the type used in surface-probe microscopes (SPMs), thereby combining the topography-sensing capacity of the SPM with measurements of electrical impedance.

In further embodiments, an array of probes can be assembled to allow simultaneous measurements with different electrical or chemical sensitivities, in scanned applications as well as fixed applications.

A probe according to specific embodiments provides one or more of the following advantages: (a) reducing the stray spurious capacitance associated with other approaches, (b) allowing a much larger range of impedance values to be quantitatively measured than other approaches, (c) yielding much higher (~ nanosecond) temporal resolution, (d) allowing measurements to be performed at much higher speeds, and (e) allowing much higher spatial resolution to be achieved.

While example probes according to specific embodiments of the present invention are described herein as used for performing various biological or chemical assays or monitoring, it will be understood to those of skill in the art that a detector according to specific embodiments of the present invention can be used in a variety of applications. These applications include, but are not limited to: monitoring ion concentration, counting micrometer- and nanometer-scale beads in gases or fluids, counting or detecting biological cells or viral particles, etc.

The invention and various specific aspects and embodiments will be better understood with reference to drawings and detailed descriptions provided in this submission. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include different innovative components and innovative combinations of innovative components and known components. No inference should be taken to limit the invention to combinations containing all of the innovative components listed in any illustrative embodiment in this specification.

In some of the drawings and detailed descriptions below, the present invention is described including various parameters of dimension and/or other parameters. These should be understood as illustrating specific and possible preferred embodiments, but are not intended to limit the invention. Many devices and/or methods have variations in one or more of the detailed parameters described herein will be apparent to persons of skill in the art having the benefit of the teachings provided herein and these variations are included as part of the present invention.

All references, publications, patents, and patent applications cited and/or provided with this submission are hereby incorporated by reference in their entirety for all purposes.

BRIEF DESCRIPTION OF THE DRAWINGS

FIG. 25 is a block diagram showing a representative example logic device in which various aspects of the present invention may be embodied.

FIG. 26 (Table 1) illustrates an example of diseases, conditions, or statuses for which substances of interest can be evaluated according to specific embodiments of the present invention.

DETAILED DESCRIPTION OF SPECIFIC EMBODIMENTS

1. Overview

Figure 1:
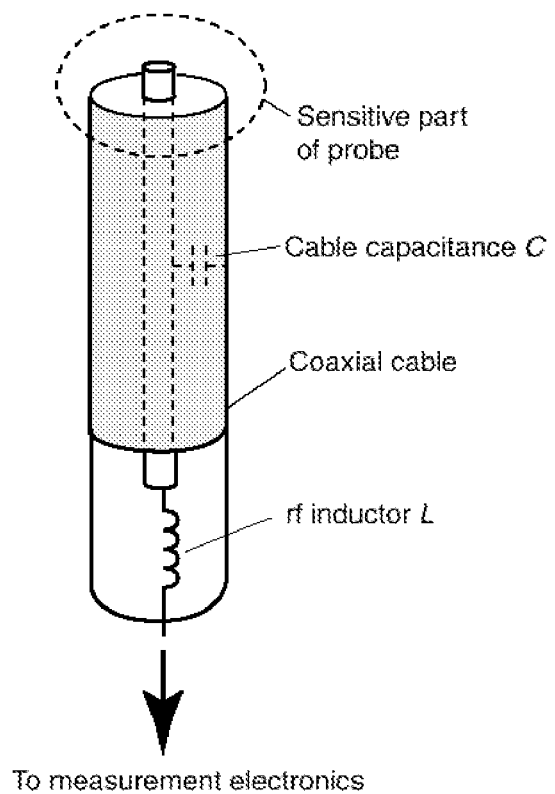
FIG. 1 is a schematic of a simple implementation of a coaxial-based resonant microwave resonance probe according to specific embodiments of the invention.

There has been extensive work in developing radiofrequency scanned probes for measuring proximal impedances in air (i.e., non-fluidic probes) (Anlage, Chamberlin, van der Weide). These typically involved using the end of a coaxial cable connected directly to measurement electronics. The cable is operated at a frequency such that the open cable end behaves like an open circuit, and the change of the reflection from the end of the cable due to a proximal impedance is monitored. This method has been used mainly for measuring the surface resistance of metals or other good conductors, as the effective coupling is best for proximal impedances near 50Ω.

Another approach is discussed by Xiang; this involves a microwave frequency ($10^9$-$10^{10}$ Hz) resonant cavity from which protrudes a conducting tip. The cavity resonance can be modulated by the proximal impedance, whose resonant frequency and dissipation can then be measured. However the frequency and coupling mechanism of this approach makes it generally limited to applications using good conductors as the proximal impedance source.

Probes for use in electrolytic and biological contexts have generally been restricted to very low (audio) frequencies. A standard electrolytic probe comprises individual electrodes submerged in an electrolytic fluid to measure current as a function of a cyclic voltage (cyclic voltammetry). A number of other measurements, essentially variations on this theme, also exist. This approach has very high current sensitivity, and allows characterization of redox potentials as well as electrolytic activity. The technique is limited in signal-to-noise by a large capacitive signal from the electrolytic fluid, and is relatively slow as well, in part due to the capacitance from the fluid and large electrical resistances in the fluid, in part due to the circuit used to excite and measure the electrochemical response.

A scanned electrochemical tool is discussed by Bard, using a mostly-insulated scanning tunneling microscope (STM) tip which is scanned over a sample submerged in electrolyte, with a large reference electrode submerged in the same electrolytic fluid. A voltage is applied between the STM tip and the reference electrode, and changes in the current flowing between the tip and reference electrode are monitored. The current is affected when the tip is passed through a region of high ionic concentration, or when it is in close proximity to a solid submerged in the electrolyte. As the tip is scanned over a surface, the response can be used to generate an image. Roughly nanometer-scale image resolution can be achieved, but high electrical impedance levels and large stray capacitances due to the electrode geometry limit the signal's temporal resolution and speed of image acquisition. Consequently, this technique cannot be used to measure rapid (less than about 1 millisecond) changes in chemical or biological processes.

A scanned ion conductance microscope has also been developed by Hansma. This comprises a glass tube filled with an ionic fluid into which an electrode is placed. A counter electrode is situated in the ionic fluid in which the ion channel-bearing membrane is placed. The glass tube has a very small opening at one end that determines the spatial resolution. The tube is scanned over the membrane allowing imaging of the local ionic concentration. It is not believed that this technique has been demonstrated at sub-micron size scales, and the speed and temporal resolution are limited again by large impedance values and large stray capacitance.

2. A Resonant High-Speed Microscopic Impedance Probe

An example individual microscopic impedance probe according to specific embodiments of the invention comprises a conducting inner probe electrode, an insulating portion, and one or more conducting shield electrodes, the latter generally connected to an effective electrical ground of the entire instrument. In specific embodiments, the probe electrode is enclosed by the grounded shield except for a small aperture or opening, near which is placed a material for which an electrical impedance is to be measured. The inner electrode is connected to one end of an inductor, whose other end is connected to a coaxial cable or other conducting structure leading to excitation and/or measurement electronics. The probe's electrical response, as measured by the electronics, is then sensitive to changes in the local electrical impedance (both phase and amplitude, or real and imaginary parts), presented by a proximal conductor, semiconductor or insulator, in solid or fluid form.

The use of an inductor, in concert with the capacitance between the probe and grounded conductors in the detecting end of the probe, creates an electrically resonant circuit whose resonance frequency can be designed to be in the audio to microwave frequency range. The resonance frequency is shifted by changes in the imaginary part of the proximal (local) electrical impedance, and the loss in the resonance affected by changes in the real part of the local impedance, allowing a measurement of both parts of the impedance. Measurements are made by exciting the probe with electrical signals at one or more excitation frequencies f, and monitoring the fraction of the radiofrequency power reflected from the probe, a quantity termed the reflectance denoted by "$S_1$", and monitoring any combination of the absolute reflectance $Abs[S_1]$, the real part of the power $Re[S_1]$, or the imaginary part $Im[S_1]$, as a function of excitation frequency f and time t. The frequency of measurement is controlled by the excitation electronics. The resonant nature of the circuit also allows high-speed measurements, as the changes in impedance can be detected at a speed of order the inverse bandwidth of the resonant circuit.

In a different application, the probe can be submerged in an electrolytic solution to allow measurements of the local electrical conductivity of the solution, for example in close proximity to a material undergoing redox reactions with the electrolyte. Furthermore, the probe can be used for monitoring the behavior of natural or synthetic ion channels in membranes, in either a biologically or chemically relevant environment, allowing dynamic measurements and imaging of ion channels in a non-intrusive manner. In addition the probe can be used to monitor the presence, motion, or quantity of particles such as biological cells, viral particles, or plastic or metallic beads in a fluid.

The probe can be used either as a standalone device, or can be fabricated with or attached to a surface-probe microscope (SPM) tip, such as a cantilevered tip of the type commonly used for atomic force microscopy. In the latter implementation, the combined instrument allows the simultaneous measurement of local electrical impedance and surface topology.

The probe can also form one element of an array of probes, designed to operate with different electrical or chemical sensitivities, allowing simultaneous measurements of a number of different properties of the material or electrolyte at the same time.

First Example

In one example coaxial geometry, such as shown in FIG. 1, an inner probe electrode is generally a metal or other good conductor (e.g., gold, silver, platinum, copper, or any other good conductor, possibly chosen based on the particular application) and is separated from the shield electrode(s) by an insulator. The shield is also made using a good conductor. One end of the coaxial geometry is exposed, and forms the detecting end of the probe. The other end of the inner electrode is connected to an inductor, and the other end of the inductor is in turn connected to a transmission line (such as a 50Ω characteristic impedance coaxial cable) that goes to measurement and or signal generating electronics.

Thus, in one example embodiment, the invention comprises a center conductor shielded except at one end by a coaxial shield. The center conductor is connected to a radiofrequency inductor that is in turn connected to measurement electronics and/or signal generating electronics. Both constant and alternating voltages can be applied to the probe, allowing measurements from dc to microwave frequencies. The impedance-matching properties of the inductor with the capacitance between the inner conductor and shield give an impedance transformation that allows high impedances to be measured at microwave frequencies by monitoring the reflectance $S_1$.

In specific example embodiments, the shield effectively encloses the inductor, which is particularly desirable where the inductor might couple electrostatically to the target, giving variable responses, for example if for some reason the inductor needs to be submerged in fluid. In other embodiments, other placements of the inductor are possible. The shield is effectively coupled to the ground of the transmission line. The length of coaxial conductor on the functional probe side of the inductor is kept to a minimum (a few millimeters), to minimize the capacitance between the inner and outer conductors, and is generally much less than a wavelength at the excitation frequency; it therefore presents an impedance corresponding to the stray capacitance C between the two conductors. This resonates with the inductor L, forming an LC resonant tank circuit with resonance frequency $f_0 = (1/2\pi)(1/LC)^{1/2}$.

According to specific embodiments of the invention, the resonance frequency can be designed to be anywhere from audio to microwave frequencies.

If one measured the absolute reflected power from an ideal LC circuit connected through a lossless 50Ω transmission line to measurement electronics, one would find that all of the incident power is reflected, and the absolute reflectance Abs[$S_1$] is independent of frequency, for any length transmission line, even as the frequency is swept through the resonance frequency $f_0$ (there is however a phase shift in the reflected signal, which yields a frequency dependence to the real and imaginary parts of the reflectance Re[$S_1$] and Im[$S_1$]). This is the zero-loss reflectance.

An inductor L however generally has a small series resistance r. The measured reflectance $S_1$ will then display a Lorentzian dip centered at the resonance frequency $f_0$, with amplitude determined by r as can be seen in FIG. 4.

Thus, according to specific embodiments of the invention, when a sample (or load) is placed near the detecting end of the probe, so that the sample couples to the electromagnetic fields emanating from the probe end, the effective capacitance and resistance of the sample (or load) impedance change the reflectance $S_1$. The capacitive part of the sample impedance ($C_L$) to a first order changes the resonance frequency $f_0$, i.e. the location of the minimum in Abs[$S_1$], and the resistive part ($R_L$) changes the magnitude (depth) of the minimum in Abs[$S_1$].

Figure 4:
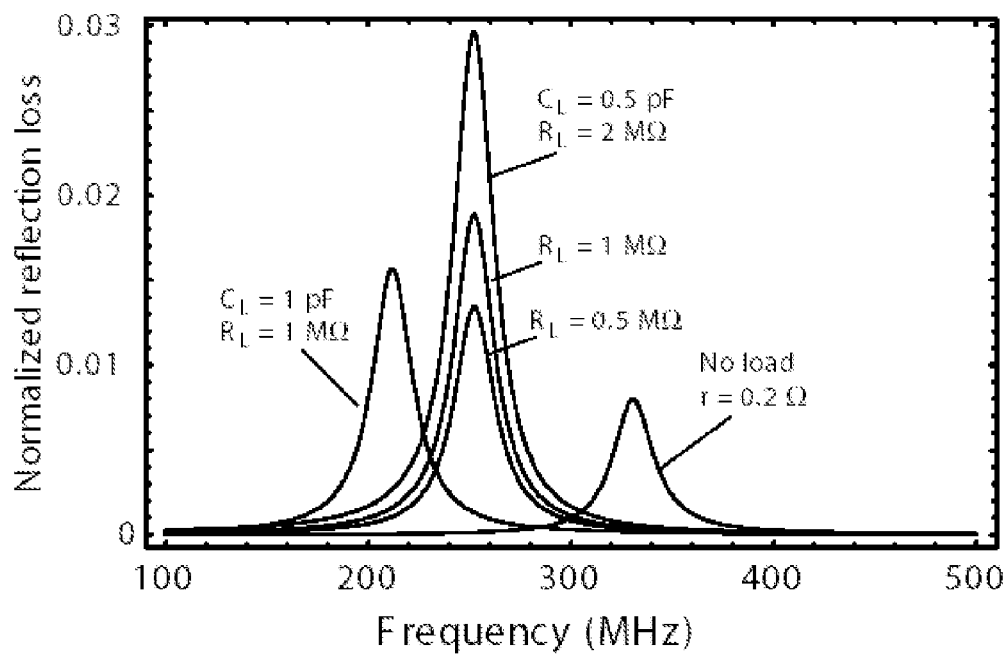
FIG. 4 is a graph showing the calculated absolute reflection loss $Γ=1-Abs[S_1]$ for an LC tank circuit resonator with inductor series resistance r=0.2Ω, and then for successive values of load resistance $R_L$ and load capacitance $C_L$ in parallel with the resonant circuit C of a microwave resonance probe according to specific embodiments of the invention. Inset to the figure is a schematic of the model circuit with circuit elements labeled as such.

FIG. 4 shows calculated examples for varying load resistance ($R_L$) and load capacitance ($C_L$) that are effectively coupled in parallel with the stray capacitance C of the probe's LC tank circuit resonator, as it would be for a proximal sample. These are calculated for example values of an inductor L=310 nH, stray capacitance C=0.5 pF, and small series resistance r=0.2 ohms. The sensitivity of the reflection to the load capacitance and resistance, even for very high load resistance (e.g., $R_L$=1 MΩ) and small load capacitance (e.g., $C_L$ less than 1 pF), is illustrated in the figure and is sufficient to provide a variety of useful sample measurements as described herein.

While monitoring the magnitude of the absolute reflectance Abs[$S_1$] at the reflectance minimum, and the change in the frequency at which the minimum occurs, delta-f, is sufficient for many measurements of interest, it is also possible to detect the real and imaginary reflectance Re[$S_1$] and Im[$S_1$] of the reflected signal as a function of frequency. In some cases it may occur that there is data in the real and imaginary parts of the reflectance that is more easily extracted than from the frequency change delta-f and reflectance magnitude data, in which case detecting the real and imaginary parts of the reflectance can be used to determine that data.

The resonant circuit parameters can be measured using external electronics. One choice is to use a vector network analyzer, which allows measurement of the real and imaginary parts of the reflected power as a function of excitation frequency. This measurement can then be used to extract the sample resistance and capacitance, in other words the real and imaginary parts of the impedance for conductors, insulators or ion-bearing electrolytic fluids.

Figure 3:
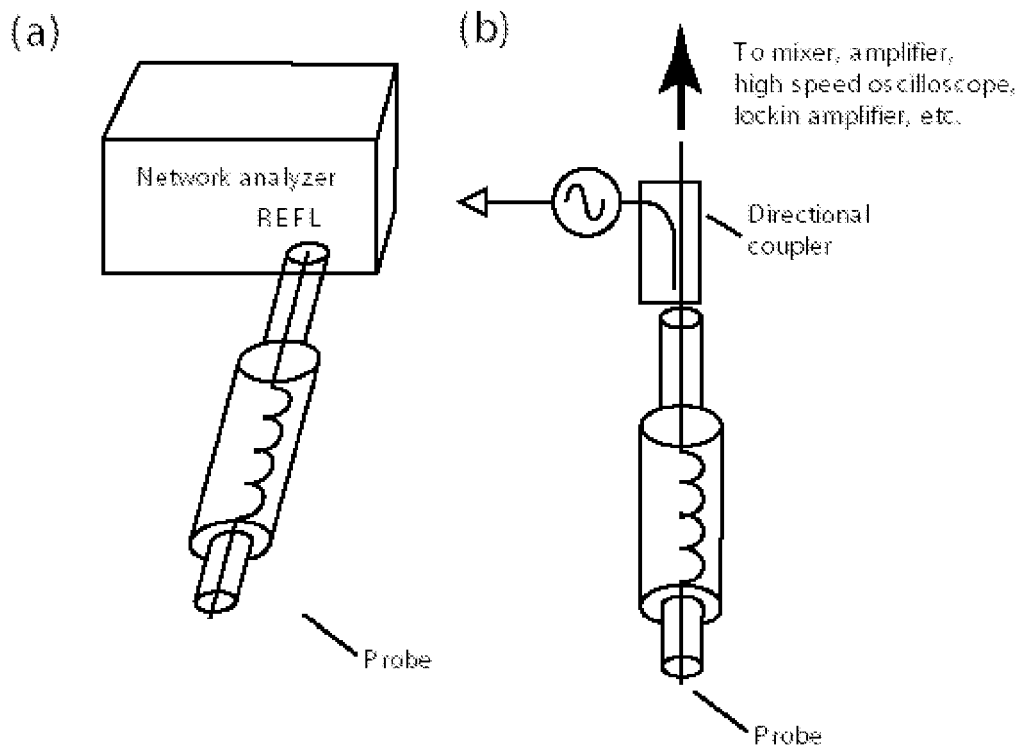
FIGS. 3 A & B are schematics showing a resonant LC tank circuit with probe coupled to measurement electronics according to specific embodiments of the invention, with A illustrating a probe coupled to a network analyzer and B showing a probe coupled to a radiofrequency source through a directional coupler, with the reflected signal routed to any number of rf detector and signal processing instruments, allowing measurement of $S_1$.

In an alternative embodiment, the resonant LC probe can be excited by a radiofrequency signal coupled through a directional coupler, and the reflected signal monitored using a number of different electronic circuits, e.g. a mixer, a radiofrequency lock-in amplifier, or an amplifier preceding a microwave frequency oscilloscope (see FIG. 3). Such circuits allow the real-time monitoring of changes in the real and imaginary parts of the proximal impedance, with a temporal resolution of the order the inverse of the width of the circuit resonance dip. In FIG. 4 for example the width is of order 30-50 MHz and corresponds to a temporal resolution of about 20 nanoseconds, but much larger widths and smaller.

Thus, according to specific embodiments of the invention, with no sample in the probe vicinity, the resonance frequency (minimum in Abs[$S_1$]) is $f_0$, with intrinsic or stray capacitance $C_0$ and the selected series inductance is L; then $f_0 \approx 1/2\pi(LC_0)^{1/2}$. If the sample is then introduced in the probe vicinity, the added sample capacitance (assuming it is not too large) can then be calculated by measuring the frequency $f_{min}$ at which the new minimum in the reflectance Abs[$S_1$] occurs, using: $L(C_L+C_0)=1/(2\pi f_{min})^2$ The sample resistance $R_L$ does not depend in a simple, monotonic fashion on the width of the resonance minimum or the magnitude of the dip in the absolute reflectance, but it can be extracted in a straightforward fashion from modeling calculations.

Determining $R_L$ and $C_L$, Using a Vector Network Analyzer

In general, analysis of the tank circuit measurement reflection to determine the exact values of the load parameters (such as $R_L$ and $C_L$) can be complex, but this analysis is well known in the art of reflectance response circuit and transmission line analysis. While various methods and approximations can be adapted to this circuit analysis, some example methods for making such a calculation are provided here for completeness of this disclosure. Any other methods for determining or estimating load values of circuits as described herein can be used in specific embodiments of the invention.

As further illustration of one such technique, consider a transmission line with impedance $Z_0$ coupled to a tank circuit that comprises a series inductor L with intrinsic stray capacitance C as illustrated in FIG. 2A. Typically, there is no resistance in parallel with the stray capacitance, in the absence of a sample in the probe vicinity. The sample load can be modeled as a parallel capacitance $C_L$ and resistance $R_L$.

Figure 2:
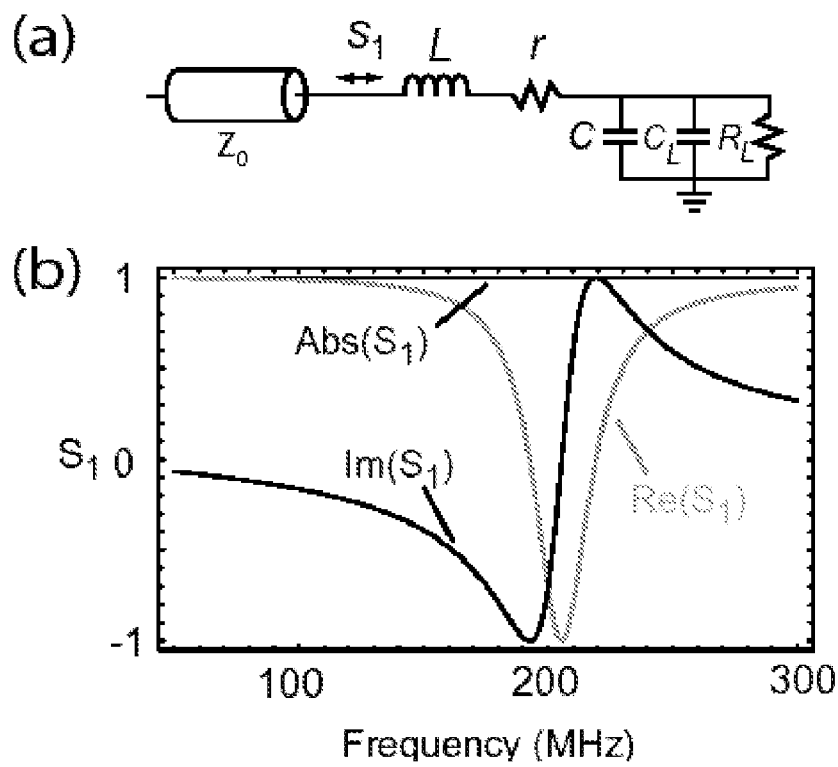
FIG. 2A is a schematic circuit diagram showing a transmission line with impedance $Z_0$ coupled to a LC resonant tank circuit that comprises a series inductor L with intrinsic stray capacitance C and with a sample load modeled as a parallel capacitance $C_L$ and resistance $R_L$. A small resistance r is included to allow for loss in the inductor or other parts of the circuit. B illustrates the calculated absolute reflectance Abs $[S_1]$ as a function of frequency f for no load, i.e. with $R_L$ set to infinity, with an example tank inductor L=300 nH, and capacitance $C+C_L=2$ pF.

The reflectance $S_1$ from the circuit is $S_1=(Z_L-Z_0)/(Z_L+Z_0)$, (1), where $Z_L$ is the frequency-dependant load impedance, $Z_L=i\omega L+1/i\omega(C+C_L)+1/R_L$ (2), where $\omega=2\pi f$ is the radial frequency in terms of the frequency f FIG. 2 B shows the calculated reflectance $S_1$ for no load, with a tank inductor L=300 nH, and capacitance $C+C_L$=2 pF. It is generally characteristic of such a circuit that with no load ($R_L \to \infty$), the reflection $S_1$ has a frequency-independent magnitude Abs[$S_1$]=1. Furthermore, with no load, the real part of $S_1$, Re[$S_1(\omega)$], goes to 1 at low and high frequencies, and has a minimum at the tank resonance frequency $\omega_0=2\pi f_0=1/(LC)^{1/2}$, with Re[$S_1(\omega_0)$]=−1 (in the example in FIG. 2 B, the resonant tank frequency is near 200 MHz.). The two $R_L \to \infty$ zero-crossing points of Re[$S_1$] give the characteristic width of the resonance, which is when the frequency c satisfies $$\left(\frac{\omega}{\omega_0}\right)^2 \mp Z_0 \sqrt{\frac{C}{L}} \left(\frac{\omega}{\omega_0}\right) - 1 = 0. \qquad (3)$$

For a cable impedance $Z_0$ much smaller than the characteristic tank circuit impedance, defined as $Z_T=(L/C)^{1/2}$, the solutions to this equation are at $\omega=\omega_0 \pm \Delta\omega_{1/2}$, where the half-width frequency $\Delta\omega_{1/2} \approx Z_0/2Z_T$, so the full width of the real resonance is $\Delta\omega=2\Delta\omega_{1/2} \approx Z_0/Z_T$. The imaginary part of $S_1$, Im[$S_1$], complements the real part, as it is the Kramers-Kronig conjugate of Re[$S_1$].

One method for determining the absolute resistance $R_L$ and capacitance $C_L$ of a load connected to the tank circuit, uses the vector (absolute value and real part) of the reflection ($S_1$) as a function of frequency: Abs[$S_1(\omega)$] and Re[$S_1(\omega)$].

Assume the lumped inductance L and stray capacitance C are known from the circuit design, and the transmission cable or path has characteristic impedance $Z_0$. Furthermore, assume the circuit measurement is properly constructed and calibrated so that:

1. If the tank circuit with load is replaced by a matched resistor $R=Z_0$, the absolute value of the reflectance $Abs[S_1(\omega)]$ goes to zero at all relevant frequencies (as does the real part $Re[S_1]$).

2. With the tank circuit connected but with no load, the absolute value of the reflectance $Abs[S_1(\omega)]$ remains at unity for all relevant frequencies, but the real part $Re[S_1(\omega)]$ exhibits the resonance displayed in FIG. 2B.

3. With the tank circuit and load connected, at high frequencies (well above the tank circuit resonance frequency), the absolute value of the reflectance $Abs[S_1(\omega)]$ goes to 1, and the real part $Re[S_1(\omega)]$ goes to $-1$.

In this case, $R_L$ and $C_L$ can be determined or estimated as follows.

1. With the load connected, determine if the absolute value of the reflection as a function of frequency $Abs[S_1(\omega)]$ has a minimum ($\omega_{min}$) at a frequency greater than zero, by, for example, using a network analyzer with a frequency scanning output to sample the reflection of the circuit over a range of frequencies.

2. If there is a non-zero minimum ($\omega_{min}$), then the resistance $R_L$ is greater than about half the tank circuit impedance, $R_L > Z_T/2 = (\frac{1}{2})(L/C)^{1/2}$. If the minimum is at zero frequency, then the resistance is smaller than this value.

3. If the resistance is greater than half the tank circuit impedance, make a first estimate of the load resistance $R_L$ and capacitance $C_L$ using $C_L \approx 1/L\omega_{min}^2 - C$.

4. If the resistance is greater than half the tank circuit impedance, $R_L$ can be estimated from the value of $Re[S_1(\omega_{min})]$. First calculate the optimal load resistance $R_{opt} = Z_T'^2/Z_0$, where $Z_T'$ is the tank circuit impedance including the load capacitance, $Z_T' = (L/(C+C_L))^{1/2}$. The dependence of $Re[S_1(\omega_{min})]$ on $R_L$ is closely approximated by: $Re[S_1(\omega_{min})] \approx (R_{opt}-R_L)/(R_{opt}+R_L)$ (5), which can be inverted to yield $R_L \approx [(1-Re[S_1(\omega_{min})])/(1+Re[S_1(\omega_{min})])] R_{opt}$. (6).

Figure 5:
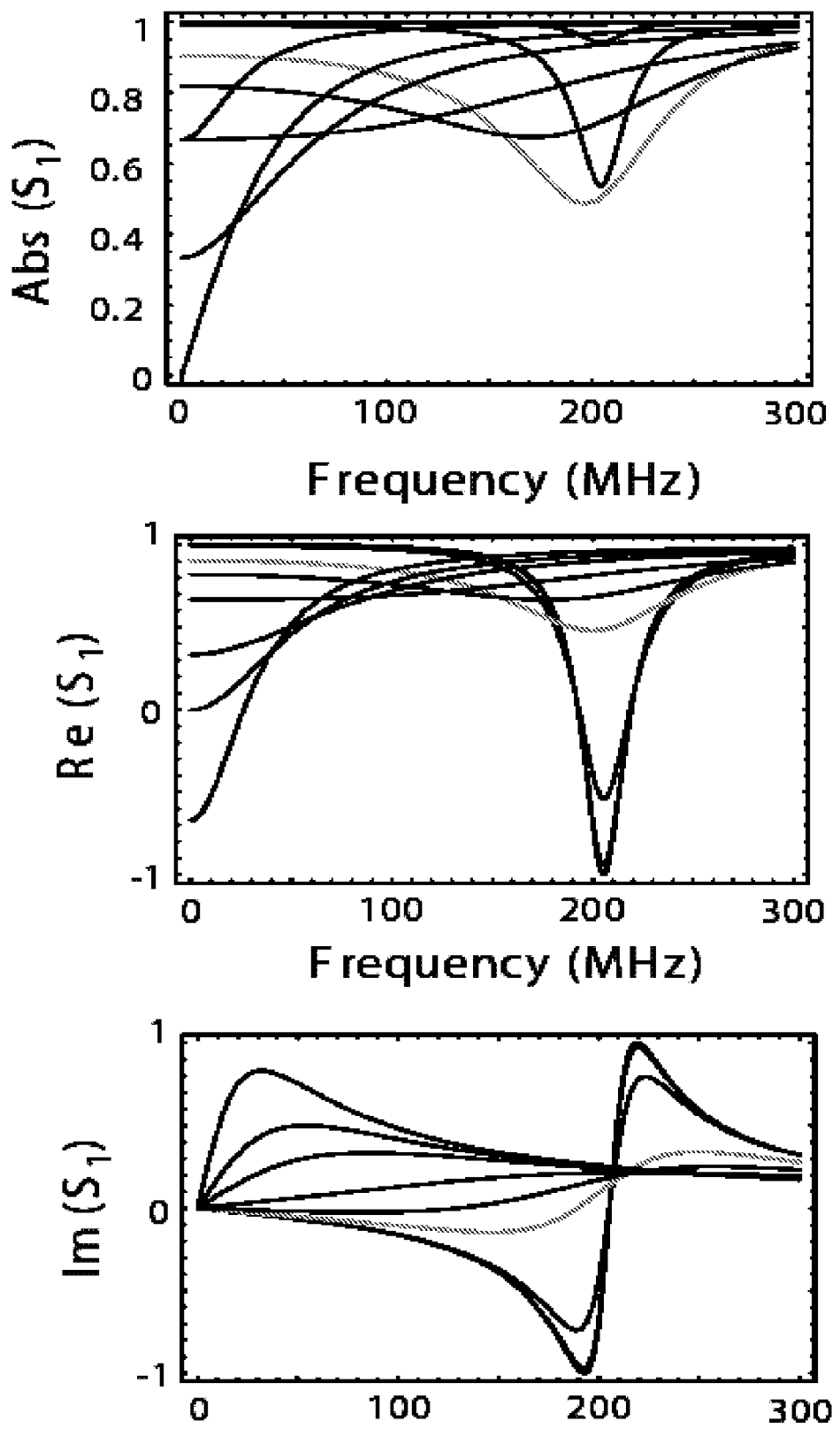
FIG. 5 is a graph illustrating example $Abs[S_1]$, $Re[S_1]$ and $Im[S_1]$ as a function of frequency for different load resistances, with $R_L=\sqrt{}$, $10^5$, $10^4$, $10^3$, 500, 250, 100, 50, 10Ω. In this example, L=300 nH and $C+C_L=2$ pF.
Figure 6:
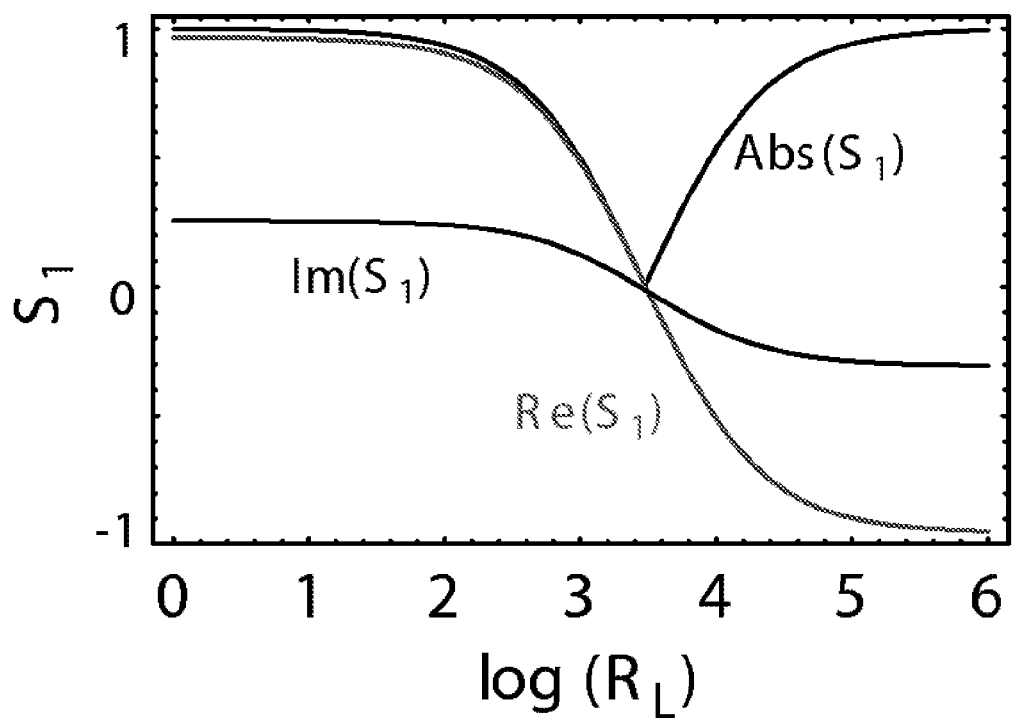
FIG. 6 is a graph illustrating example $Abs[S_1]$, $Re[S_1]$ and $In[S_1]$ at a fixed frequency $f=1/(2π(LC_t))$, as a function of load resistance $R_L$. In this example, L=300 nH and $C_t=C+C_L=2$ pF.

If the resistance is less than half the tank circuit impedance, or if a more precise determination of the resistance is desired, or if a vector measurement of $S_1$ is not available and only the magnitude $Abs[S_1]$ can be measured, then a least-squares curve fit of $Abs[S_1(\omega)]$ to a measured response as a function of frequency can be used. For the simple load model circuit of a parallel resistance $R_L$ and capacitance $C_L$, connected to a tank circuit through an inductor L with stray capacitance C, the impedance $Z_L$ of the tank circuit and load is given by load impedance, $Z_L = i\omega L + 1/i\omega(C+C_L) + 1/R_L$, and the absolute value of the reflectance is given by $Abs[S_1] = |Z_L - Z_0|/|Z_L + Z_0|$. Standard mathematical techniques can be used to least-squares match the calculated value of $Abs[S_1(\omega)]$ to that measured, using $R_L$ and $C_L$ as the free parameters in the fit, and in this way an absolute value for these two parameters can be accurately determined. As examples of the underlying data for such a curve fit, see FIG. 5 and FIG. 6.

3. Varactor Tuning of Impedance Matching Circuit

In a further embodiment, the shielded RF probe described above can employ a varactor (variable diode capacitor, an electronically controlled circuit element) in parallel with the device. In example implementations of this embodiment, the invention has regularly achieved a reflectance of $-90$ dB, a device impedance matched to of order 1 part in $10^9$ to the cable impedance, which is typically 50 ohms. This implementation dramatically increases the device performance in various specific situations and implementations.

The performance of the RF impedance probe described above depends sensitively on how well an impedance match can be achieved between the probe and the electronics connected to it. This impedance match is achieved in part by the inductance placed in series with the probe, an inductance that resonates with the intrinsic capacitance of the probe. The electronics are typically connected to the device using a 50 ohm cable, and the electronics themselves impedance matched to $Z_0 = 50$ ohms. Impedance match of the device to the same 50 ohm impedance is achieved at frequencies near the resonant frequency $f_0 = 1/2\pi\sqrt{LC}$, where L is the inductance value (in Henries) and C the device capacitance value (in Farads), yielding the resonant frequency $f_0$ (in Hertz; note we also use the resonant radial frequency $\omega_0 = 2\pi f_0$). At or near this frequency, the device (including the inductance) presents to the rest of the circuit an impedance Z, and the reflectance of RF power from the device is $$\rho = \frac{Z - Z_0}{Z + Z_0}$$

(this is the ratio of reflected to incident power). Having the ability to controllably adjust Z to equal $Z_0$ allows adjusting the reflectance to zero or very near zero. In this zero- or near zero-reflectance situation, a very small change in the device impedance Z, due to a change in the material near the end of the probe, then yields a non-zero reflectance, giving rise to an increase in the reflected power. This situation is thus a "darkfield" measurement and is favorable for very high sensitivity to very small changes in Z.

Varactor Example 1

In further embodiments, the invention according to specific embodiments involves a method or device for achieving an impedance match electronically, using an additional circuit element called a varactor diode (various configurations of which are commercially available) to achieve good impedance matching, with reflectances p ranging from 1 to as little as $10^{-9}$ to $10^{-10}$.

Figure 7:
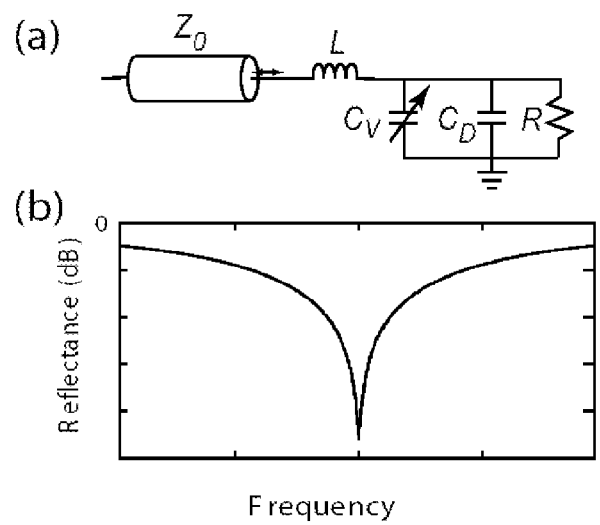
FIG. 7 (a) is a schematic of an example circuit for varactor tuned impedance matching according to specific embodiments of the invention and (b) indicates experimental reflectance measurements off an implementation of this example circuit.

FIG. 7 (a) is a schematic of an example circuit for varactor tuned impedance matching according to specific embodiments of the invention and (b) indicates experimental reflectance measurements off an implementation of this example circuit. In one example embodiment, to achieve good to excellent impedance match between the RF probe and a 50 ohm cable, using a set of discrete inductors L, and here, adding a varactor diode that acts as a controllable capacitance $C_V$. Here good to excellent means reflectances ranging from roughly 30% to as close to zero as is physically possible, limited by noise and device performance; we can typically achieve 1 part in $10^9$ or 1 part on $10^{10}$ reflectance (i.e. $\rho = 10^{-9}$ to $10^{-10}$). The schematic for the circuit is shown in FIG. 7, comprising the cable impedance $Z_0 = 50$ ohms, the inductor L, and the varactor diode tunable capacitance $C_V$. The device (probe) is modeled fairly generally as a parallel capacitance $C_D$ and resistance R (this does not include all possible impedances presentable by the probe, but matches very well a very wide range of possible situations).

Operation of this circuit according to specific embodiments of the invention can be understood as follows. At a measurement radial frequency $\omega$, the impedance of the circuit to the right of the transmission line is $$Z(\omega) = i\omega L + \frac{1}{i\omega C + 1/R}, \quad (1)$$

where I define the total capacitance $C=C_V+C_D$. For this impedance to equal the (real) impedance $Z_0$, arrive at two equations for the real and imaginary parts of $$Z: \omega = \frac{1}{RC}\sqrt{\frac{R}{Z_0} - 1}, \text{ and } \omega = \frac{1}{\sqrt{LC}}\sqrt{1 - \frac{L}{R^2 C}},$$

which must be satisfied simultaneously. The cable impedance $Z_0$ is typically fixed, the device resistance R can be varied but is typically the parameter to monitor and therefore not fully controlled, but the values of L and C are adjustable, as is the measurement frequency $\omega$. Equating these two relations to one another yields the following two results:

$$Z_c \equiv \sqrt{\frac{L}{C}} = \sqrt{RZ_0},$$

defining the characteristic impedance $Z_c$ in terms of the inductance L and total capacitance C, showing this must be equal to the geometric mean of R and $Z_0$, and $$\omega = \sqrt{\frac{1}{LC}}\sqrt{1 - \frac{Z_c^2}{R^2}},$$

giving the measurement frequency at which the perfect impedance match appears. In the usual case where $R \gg Z_0$, the second square root in the expression for the frequency is very close to 1, resulting in the approximate result $$\omega \cong \sqrt{\frac{1}{LC}}.$$

Thus, a good to excellent impedance match can nearly always be found with a smoothly adjustable characteristic impedance $Z_c$. While smoothly adjustable inductors L do exist and could be used in various embodiments of the invention, such smoothly adjustable inductors generally do not work well. Thus, in the present invention according to specific embodiments, a varactor diode is used as a tunable C, which when used with a reasonable value of L allows a good to excellent match to be achieved.

In specific embodiments, the quality of the impedance match is determined by measuring the RF power reflected from the circuit shown in FIG. 7, measured by applying an RF signal to the left end of the transmission line and measuring how much power is reflected back. The ratio of the reflected to the incident power is the reflectance $\rho$, given by $$\rho = \frac{Z - Z_0}{Z + Z_0},$$

which clearly goes to zero if the real part of Z equals $Z_0$ and the imaginary part equals zero, the condition applied above to yield the characteristic impedance and measurement frequency determining equations. Prior to the use of the varactor diode, a best impedance match in some implementations in a "typical" situation was around −30 dB, that is −30 dB=10 $\log_{10}\rho$, which translates to a mismatch $\Delta Z/Z_0 \cong 2 \times 10^{-3}$, i.e. roughly a part per thousand match. Using the varactor diode typically allows a match of about −80 to −90 dB, i.e. a mismatch $\Delta Z/Z_0 \cong 2 \times 10^{-8}$ or better, i.e. better than 1 part in 100 million. This increases the sensitivity of the device in a very significant way.

Varactor Example 2

Figure 8:
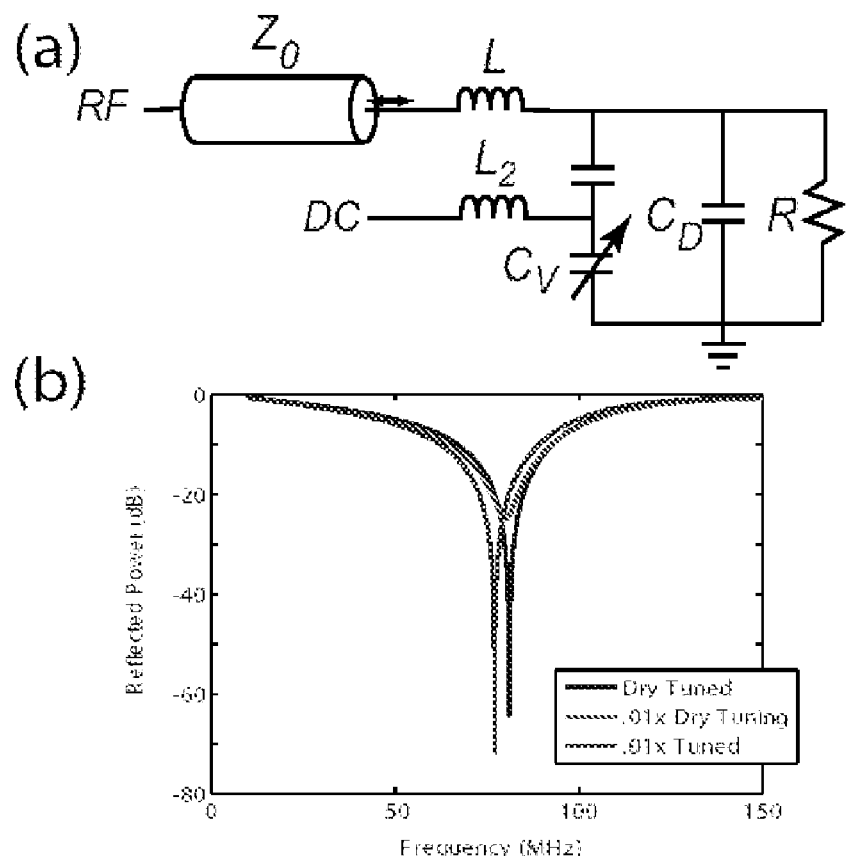
FIG. 8 (a) is a schematic of an example circuit for varactor tuned impedance matching that allows separate DC tuning of the varactor diode and RF reflectance and (b) indicates experimental reflectance measurements off a tuned circuit, showing impedance matching of better than −70 dB for two different solutions, both according to specific embodiments of the invention.

FIG. 8 (a) is a schematic of an example circuit for varactor tuned impedance matching that allows separate DC tuning of the varactor diode and RF reflectance and (b) indicates experimental reflectance measurements off a tuned circuit, showing impedance matching of better than −70 dB for two different solutions, both according to specific embodiments of the invention. This circuit allows separate DC tuning of the varactor diode (indicated as a variable capacitor $V_C$) and RF reflectance of the full circuit. The biased side of the diode is DC isolated from the remainder of the circuit by a capacitor whose value is chosen to be much larger than that of the varactor diode, and the varactor diode capacitance $C_V$ is typically of the same order as the device capacitance $C_D$. The inductor L2 allows the DC bias circuit (marked "DC") to be isolated from the RF part of the circuit. Thus, as an example of a specific implementation of this concept, the circuit of FIG. 8 enables electrical adjustment of the varactor diode, so that the capacitance it presents can be changed and the impedance of the device matched to the cable.

Electrical Measurement Temporal and Spatial Resolution

The electrical measurement bandwidth of the system is determined by the quality factor of the resonator, which for the configuration described here is given by $Q=(L/C)^{1/2}/50\Omega$, determined primarily by the cable impedance, and for most typical parameter values falls in the range of 1 to 10. The electrical measurement bandwidth $\Delta f$ is then roughly the resonance frequency $f_0$ divided by Q, and the shortest time $\Delta t$ over which changes in the load parameters (e.g. $R_L$ and $C_L$) can be resolved is the inverse of the measurement bandwidth, $\Delta t = 1/\Delta f$. A 1 GHz LC resonator with Q=5 would therefore have a measurement bandwidth of 200 MHz, allowing monitoring the load impedance with a temporal resolution (shortest measurement time) of about 5 nanoseconds.

The spatial resolution of the probe is primarily determined by the lateral dimensions (width) of the probe conductor, and the distance from the probe conductor to the shield. Experiments have shown that spatial variations in the load impedance of order one-fifth the sum of these distances can be resolved. Thus, an inner conductor with a width of 20 nm and thickness of 5 nm, with an insulator 20 nm thick, could then have a spatial resolution of about 1 to 10 nm, approaching atomic resolution. With a small diameter coaxial probe, both the very short time and very small size scale response of a conductor, semiconductor, insulator, electrolytic or ion channel process can be monitored.

Planar Geometry

A probe according to further embodiments of the invention can also be made using a planar geometry, allowing fabrication using thin films of metals and insulators, and allowing the use of precision microfabrication technology to achieve very small effective probe diameters and therefore very high spatial resolution. The conducting electrode of the probe is fabricated using a good conductor (gold, silver, platinum, copper, etc., possibly chosen to suit the particular application), patterned using lithographic techniques. State-of-the-art lithographic technology allows patterning down to lateral dimensions of about 10 nm, while more conventional optical lithography allows patterning with about a 50-100 nm size scale. The insulating layer that separates the inner electrode from the outer shield can be an insulating thin film such as silicon dioxide, silicon nitride or aluminum nitride, among a wide range of other materials. This can be patterned using the same lithographic techniques as used for the inner electrode. The outer electrode is a conductor, of the same or different composition as the inner electrode, and is also patterned using the same techniques.

Three examples for how this part of the probe can be fabricated using planar lithographic techniques are given as follows; note that someone practiced in the art can easily extend these examples to a number of other geometries and approaches, so these examples are not meant to be exclusive.

Fully Shielded Nanometer Scale Probe

Figure 9:
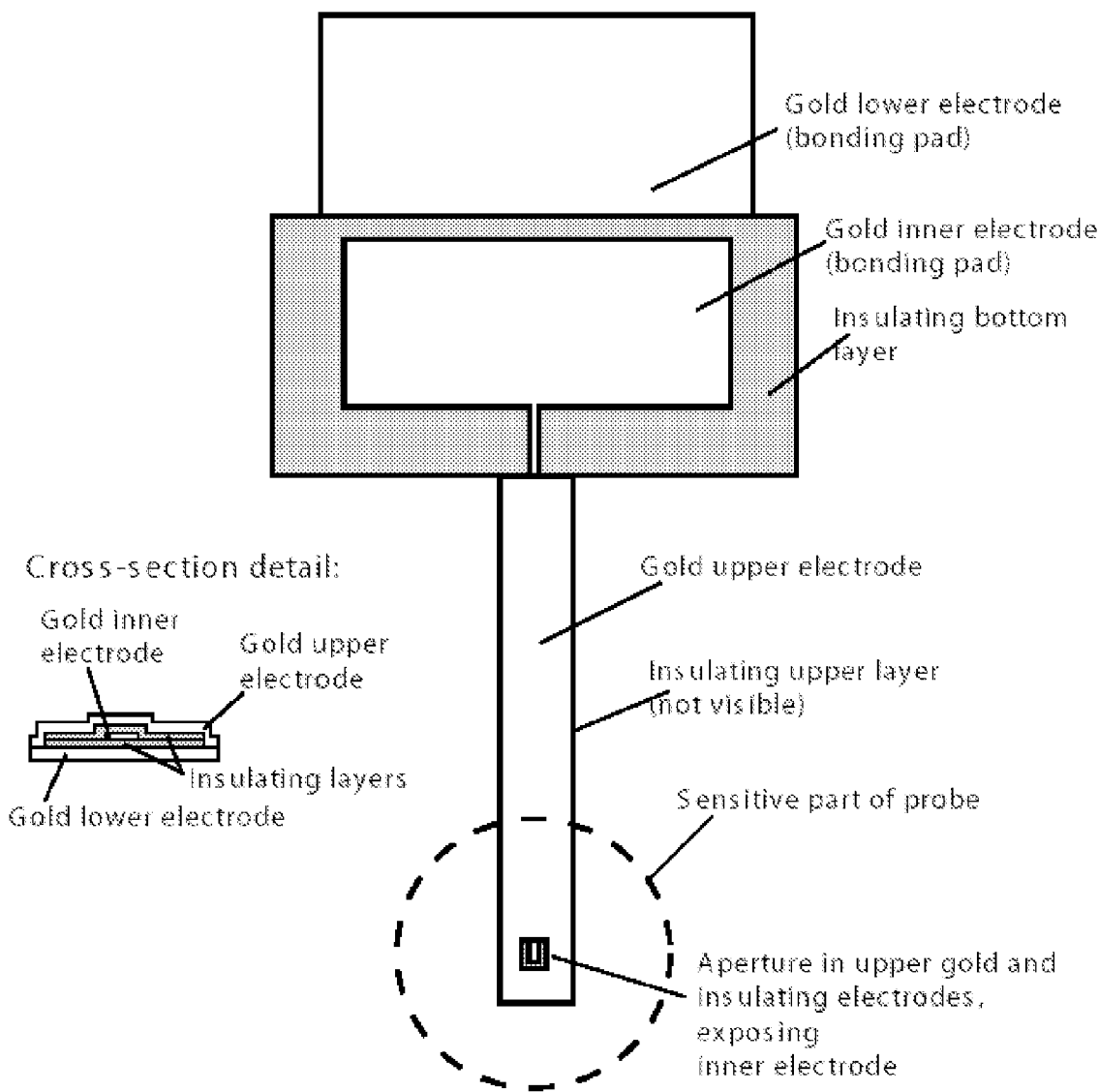
FIG. 9 is a schematic showing an example planar geometry probe according to specific embodiments of the invention.

FIG. 9 is a schematic showing an example planar geometry probe according to specific embodiments of the invention. In such an example geometry, a bottom first layer is used as part of the shield electrode, a second insulating layer provides a first part of a insulating core, a third layer provides the probe electrode, a fourth insulating layer continues the insulating core, and a fifth layer is also used as part of the shield electrode.

In the illustrated embodiments, gold is used for the three conducting layers, though as discussed elsewhere herein, any conducting material could be used. Examples of suitable conductors are discussed herein.

In this example embodiment, an aperture has been patterned in the top layer and possibly in the fourth insulating layer, exposing the inner electrode and making the structure sensitive to impedances presented near the aperture. A cross-sectional view of the layer structure is also shown.

In one example embodiment, optical lithography is used to pattern a one micrometer-wide electrode of gold 100 nm thick, forming the lower layer of shielding conductor; this strip widens at one end to a pad for wire contacts. Optical lithography is then used to pattern a 0.8 µm wide strip of silicon nitride 20 nm thick, forming the lower insulating layer, centered on the first electrode, and widening at one end for either a wire bond pad or to accommodate a spiral-wound, radiofrequency inductor (see below). Electron beam lithography is then used to pattern a 20 nm wide electrode of gold, widening at one end to a 0.6 mm wide pad, forming the inner electrode for the probe. Optical lithography is used to pattern a second, 0.8 µm wide strip of silicon nitride, 20 nm thick, forming the top insulating layer. Electron beam lithography is used to pattern a 1.0 µm wide strip of gold, 100 nm thick, to form the top shielding layer; this layer includes a 40 nm by 40 nm aperture through which the inner electrode is exposed. The upper insulating layer can also be patterned with such an aperture, if desired. This example probe would have approximately 10-20 nm spatial resolution to changes in the local electrical impedance.

Half-Shielded Micrometer Scale Probe

Here the approach is essentially the same as discussed above, but the patterning is performed using an all optical lithographic technology, wherein the first shielding layer is omitted, the inner conductor has a width of 0.2 µm, and the aperture has a width of 0.4 µm. The spatial resolution would then be about 0.1 µm. Note that in this case the assumption is that the substrate on which the probe is patterned provides sufficient decoupling from proximal impedances, due to reduced capacitance, that a full shield on the bottom surface can be omitted for fabrication simplicity.

Edge-Exposed Nanometer Scale Probe

Figure 10:
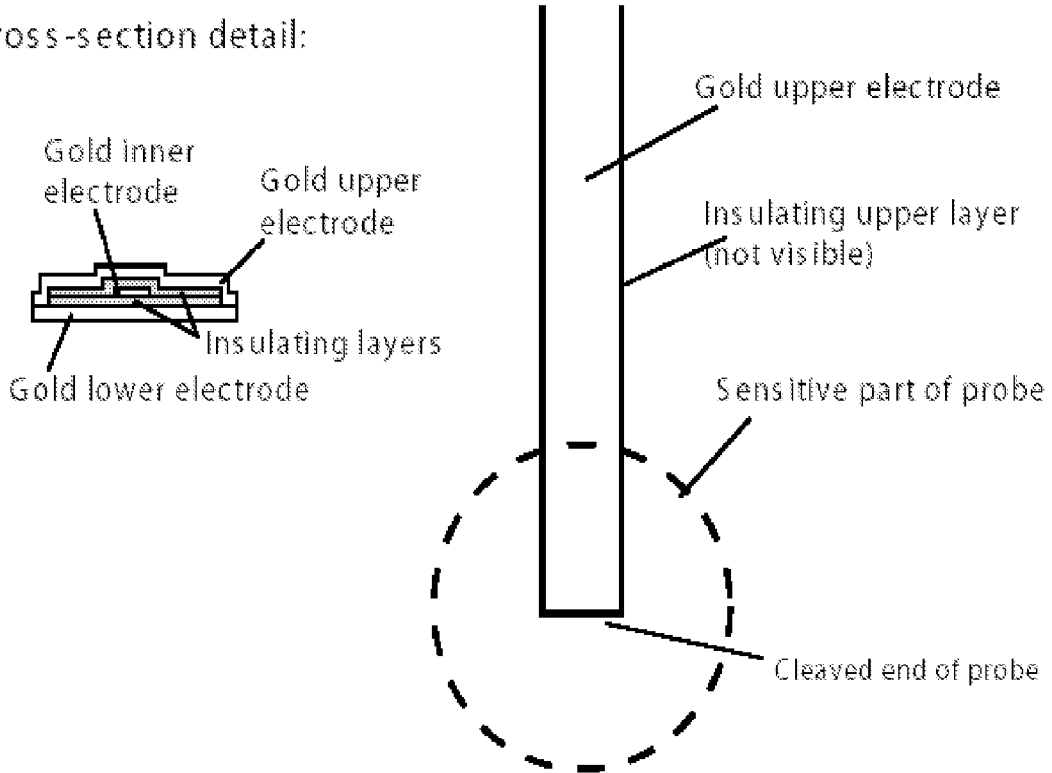
FIG. 10 is a schematic showing an example planar geometry probe similar to that shown in FIG. 9 where instead of using an aperture to expose the inner conductor, the end of the microfabricated structure is cleaved or cut open to expose the end of the layer structure according to specific embodiments of the invention.

FIG. 10 is a schematic showing an example planar geometry probe similar to that shown in FIG. 9 where instead of using an aperture to expose the inner conductor, the end of the microfabricated structure is cleaved or cut open to expose the end of the layer structure according to specific embodiments of the invention. Here the approach is essentially the same as discussed above, but instead of using an aperture to expose the inner electrode, the edge of the inner electrode is exposed by cleaving the end of the probe or by cutting using a tool such as a focused ion beam etcher, and the end of the probe is then the sensitive area, allowing a spatial resolution of approximately 1 to 5 nm in both directions.

Figure 11:
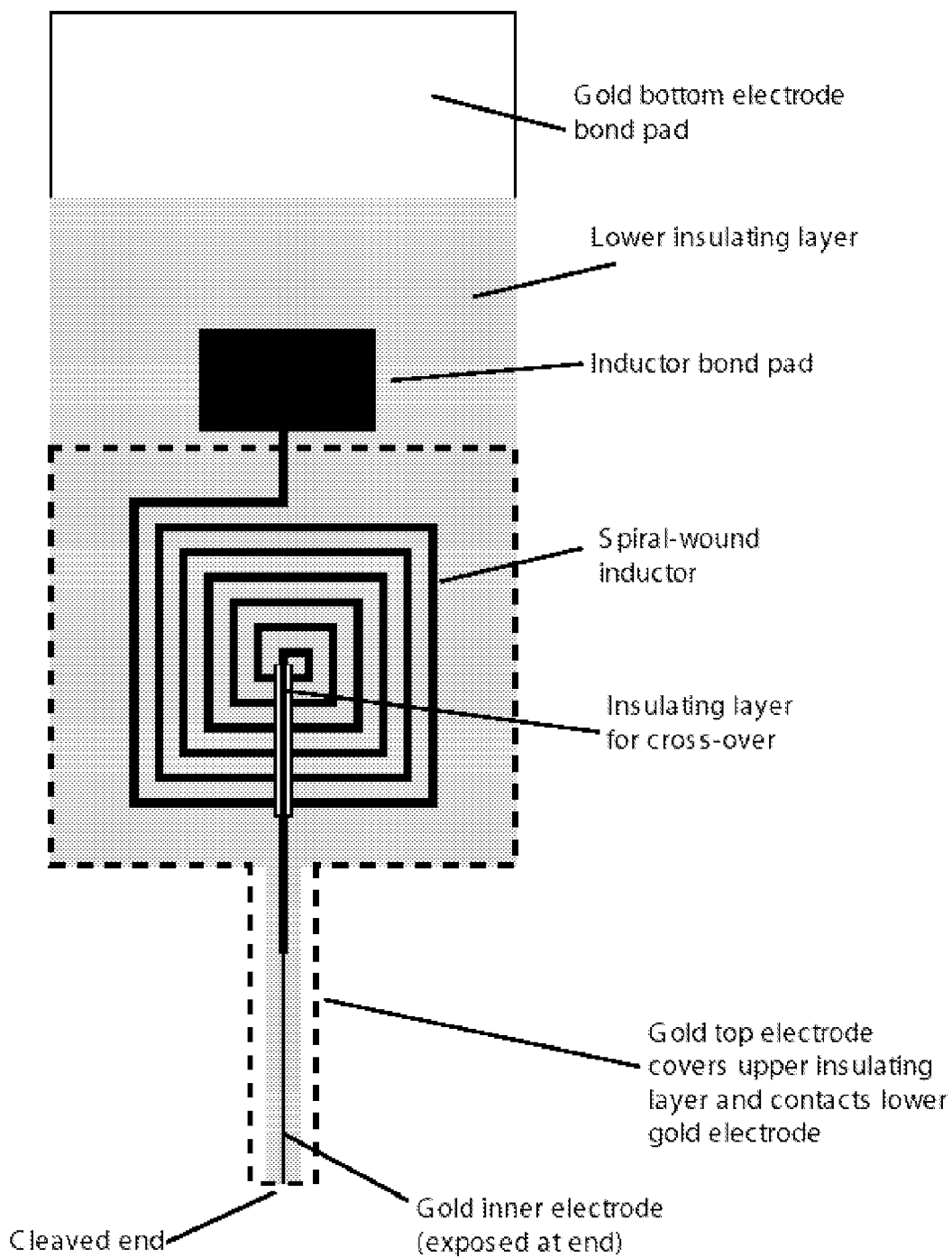
FIG. 11 is a schematic showing an example of a microfabricated, cleaved-end probe that includes an integrated inductive element, spiral-wound with an insulating cross-over according to specific embodiments of the invention where elements that cannot be seen are similar to those shown in FIG. 10.

As fabricated, the inner electrode is electrically isolated from the outer electrode, but again with a capacitance C between the two electrodes. An electrical connection is then made between the inner electrode and a radiofrequency inductor L, the latter of which can either be patterned lithographically on the same surface as the probe assembly just described, as illustrated in FIG. 11, or can be a separate component (either lithographically patterned or wire-wound on an insulating form, available commercially). The inductor L and capacitor C then form a resonant circuit exactly as described for the coaxial geometry probe shown in FIG. 11 and discussed above.

The active end of the probe in the planar geometry is formed between the inner conductor and outer shield, either where this gap is exposed using an aperture or at the exposed cross-sectional edge of the probe. In either case the substrate supporting the lithographically patterned materials would then be cut or etched using standard techniques to make a cantilevered probe that can be brought into close proximity with the material to be measured.

One reason for using a lithographed probe is that the spatial resolution can be tremendously higher, reaching 1 to 5 nm for the highest resolution lithography. In addition this approach can be used to fabricate the probe on the surface of a cantilevered tip such as is used in Scanning Probe Microscopy (SPM), yielding a fully integrated impedance and topography probe, as described below.

Figure 12:
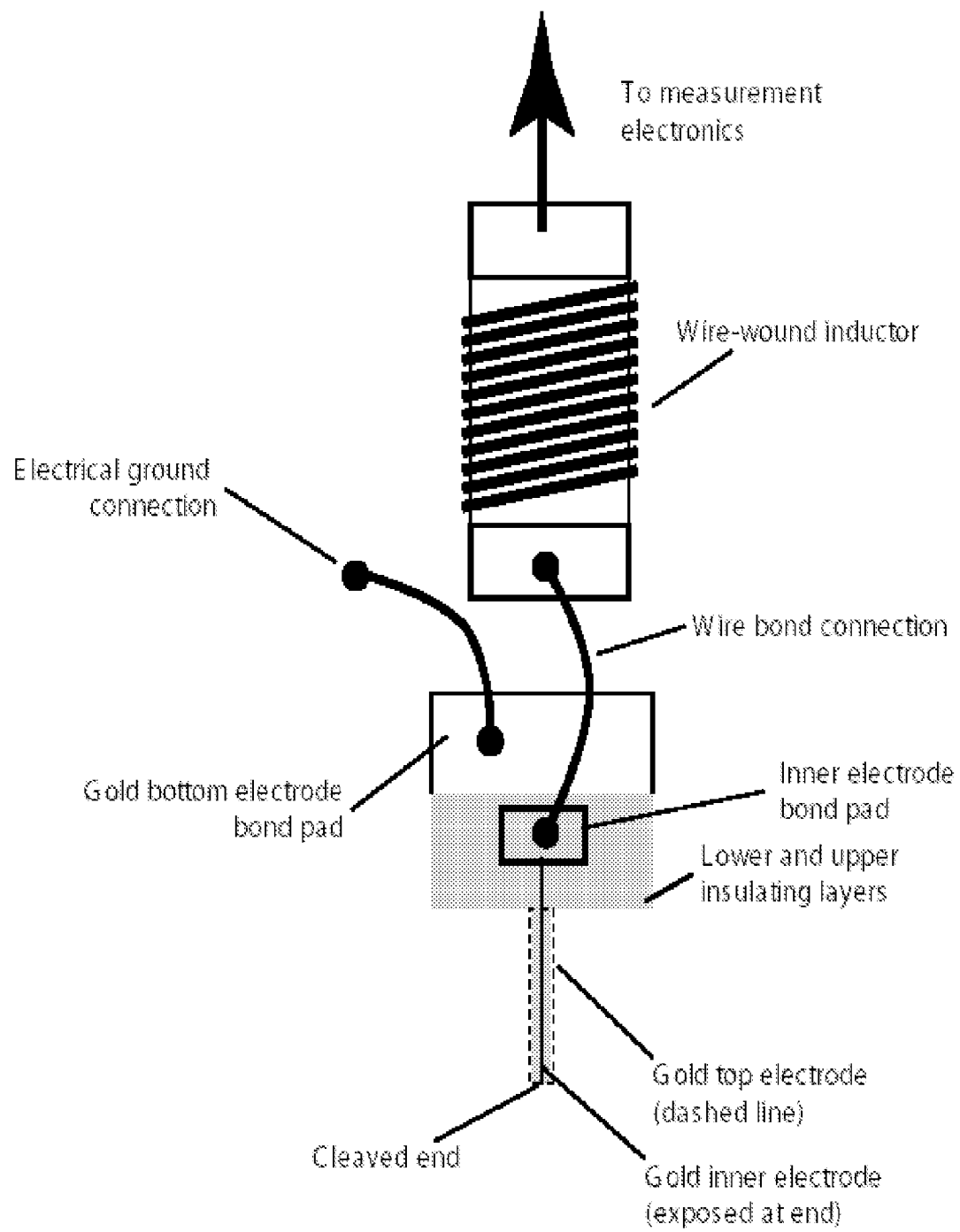
FIG. 12 is a larger scale schematic showing an example view of a structure of the form shown in FIG. 10, with a cleaved-end probe, here showing how electrical connections would be made to a discrete inductive component and to the signal ground, forming the electrically resonant circuit according to specific embodiments of the invention.

FIG. 12 is a larger scale schematic showing an example view of a structure of the form shown in FIG. 10, with a cleaved-end probe, here showing how electrical connections would be made to a discrete inductive component and to the signal ground, forming the electrically resonant circuit according to specific embodiments of the invention. It will be understood to those of skill in the art that in various implementations a discreet inductor or an integrated inductor can be selected according to specific embodiments of the invention.

Scanning Impedance Detection

A probe according to specific embodiments of the invention can be a stand-alone instrument. For example, it can be attached to a three-axis translation stage with the probe axis directed along the vertical direction, the probe brought into close proximity with a sample, and the probe can then be scanned in the two horizontal directions to generate a two-dimensional map of electrical impedance. The vertical position of the probe can be adjusted to maintain constant capacitance to the sample, and the map can then include both the resistance of the sample and the vertical adjustments. This type of scanned image generation is typically used for a SPM. Such an approach has been discussed by a number of authors (see van der Weide; Anlage; Wellstood), but these all used simple coaxial cables from which the reflection signal was monitored.

In the present invention, the use of the radiofrequency inductor allows measurements at equally high frequencies, but in addition allows probing for real impedance levels that are several orders of magnitude higher: The best coupling to a simple coaxial cable occurs when the proximal impedance is close to 50Ω, while in the probe described here, the range of easily detectable resistances can easily cover several orders of magnitude (for the circuit shown in FIG. 2, the reflection loss can be used to measure sample resistances $R_L$ from about 10Ω to $10^8$Ω).

Furthermore, in the approach used by these other investigators, the coaxial cable cannot have any additional reflections due to imperfections in the cable or transitions to lithographed structures such as described above; therefore it is difficult to fabricate lithographed, very high spatial resolution versions of those authors' instruments. In the present invention, the shielded inner conductor-shield pair does not need to have any particular properties other than to minimize the capacitance C between the two. Thus, almost any insulated pair of conductors could be operated in the resonant fashion described. It is therefore fairly straightforward according to the invention to make almost any conductor geometry, with the appropriate L and not too large a value of C, work in the fashion described.

Figure 14:
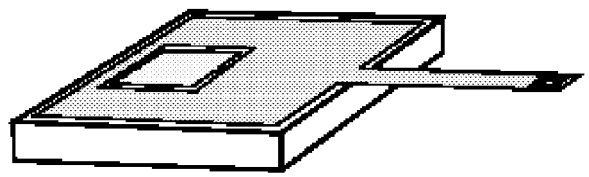
FIG. 14 is a schematic showing an example probe integrated with a cantilevered tip according to specific embodiments of the invention.
Figure 14:
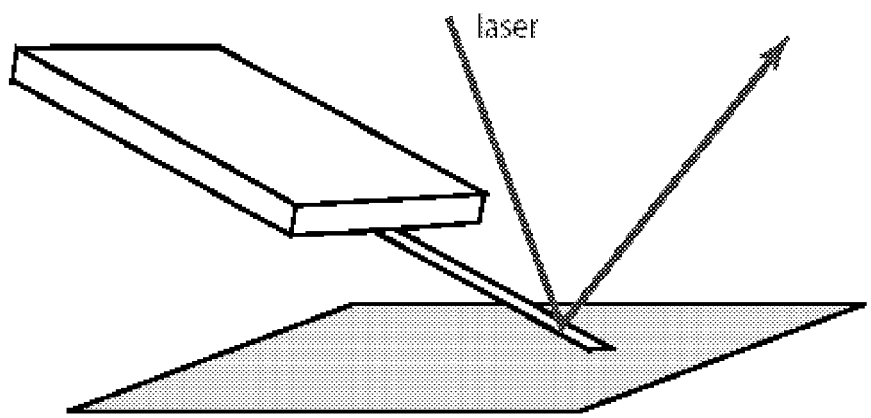
Figure 15:
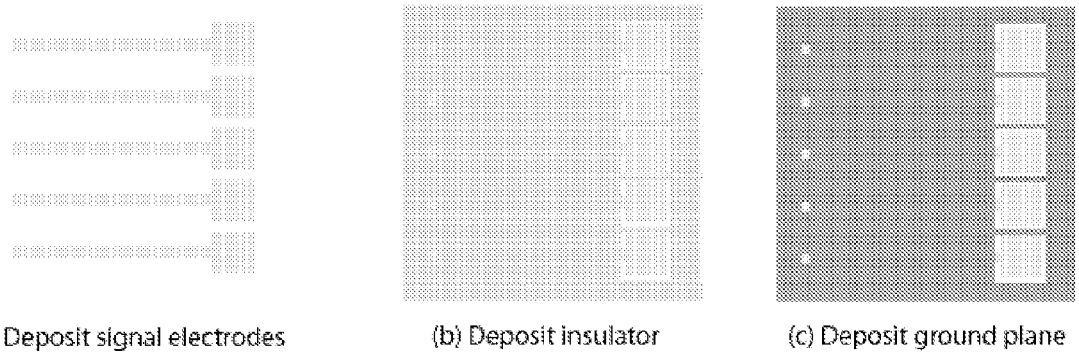
FIG. 15 is a schematic drawing showing an example of fabricating an array of probes according to specific embodiments of the invention.

FIG. 14 is a schematic showing an example probe integrated with a cantilevered tip according to specific embodiments of the invention. The probe as described can be integrated with a cantilevered tip of the type used by SPMs. An SPM cantilevered beam can be fabricated so as to include on its scanning side the inner conductor-outer shield with an aperture. By placing this integrated probe, with its measurement electronics, in a fully operational SPM, the topographic signal generated by the SPM deflection-sensing electronics can be combined with the impedance signal generated by the probe to allow simultaneous measurements of the two. Other investigators (e.g., van der Weide) have discussed using a similar arrangement but using a simple direct cable connection and without the other impedance matching benefits of the invention.

Array Impedance Detection

A probe according to specific embodiments of the invention, especially in the lithographically patterned design, can easily be configured into array geometries, either a linear (one dimensional) or a full planar (two dimensional) array. The individual probes in the array can then either be driven by a single radiofrequency source and the individual reflections measured with an array of measurement electronics (e.g. an array of radiofrequency mixers that are then multiplexed into a single data recording system such as a radiofrequency oscilloscope), or each driven with a separate radiofrequency source to avoid cross-coupling of signals. Arrayed approaches allow measurements using sensitivities to different frequencies, different geometry scales, cross-correlation of signals at different points in the sample being measured, or, in electrolytic samples, differing chemical sensitivities due to different sensitization preparation of the probe surfaces.

Varying Distance by Probe Motion

In a further modification to any of the embodiments discussed herein, the sensitivity of the probe to particles of different sizes can be adjusted by adjusting the spacing between the probe and ground or shield electrodes. Many techniques are known in the art for using piezoelectric, temperature activated, or other types of actuators to adjust the spacing of parts of integrated microfabricated devices. In specific embodiments, surfaces surrounding the probe, or the probe metallization, or both, can be deformable, so that the spacing between the probe signal and ground, for instance, can be made smaller in order to decrease the sensitive volume or change the delectability of a given analyte.

Varactor Planar Design

In further embodiment of the invention, a planar design such as shown in FIG. 9, FIG. 10, FIG. 11, or FIG. 12 can be further include a varactor operatively connected as described for example with regards to FIG. 7 or with a varactor and inductor L2 as described with regards to FIG. 8. Various techniques are know for fabricating a varactor in a solid state IC device, such as the Ion implantation method described in *Monolithic Varactor Tuned Rf Amplifier Ic Using Ion Implantation*, Manchester, K. Macdougall, J. Tkal, O. Chu, T. *Solid-State Circuits Conference. Digest of Technical Papers.* 1973 *IEEE International*, February 1973 XVI, p 186-187, and other methods know in the art. The varactor can also be fabricated on-chip with a sensor where the sensor were is based on an appropriate substrate (such as silicon or gallium arsenide.)

In some planar embodiments, a separate component varactor can be configured into the planar geometry. In further embodiments, a tank circuit according to specific embodiments of the invention includes a variable capacitor diode ("varactor") that serves as an electronically controlled tuning element to improve impedance matching.

Figure 13:
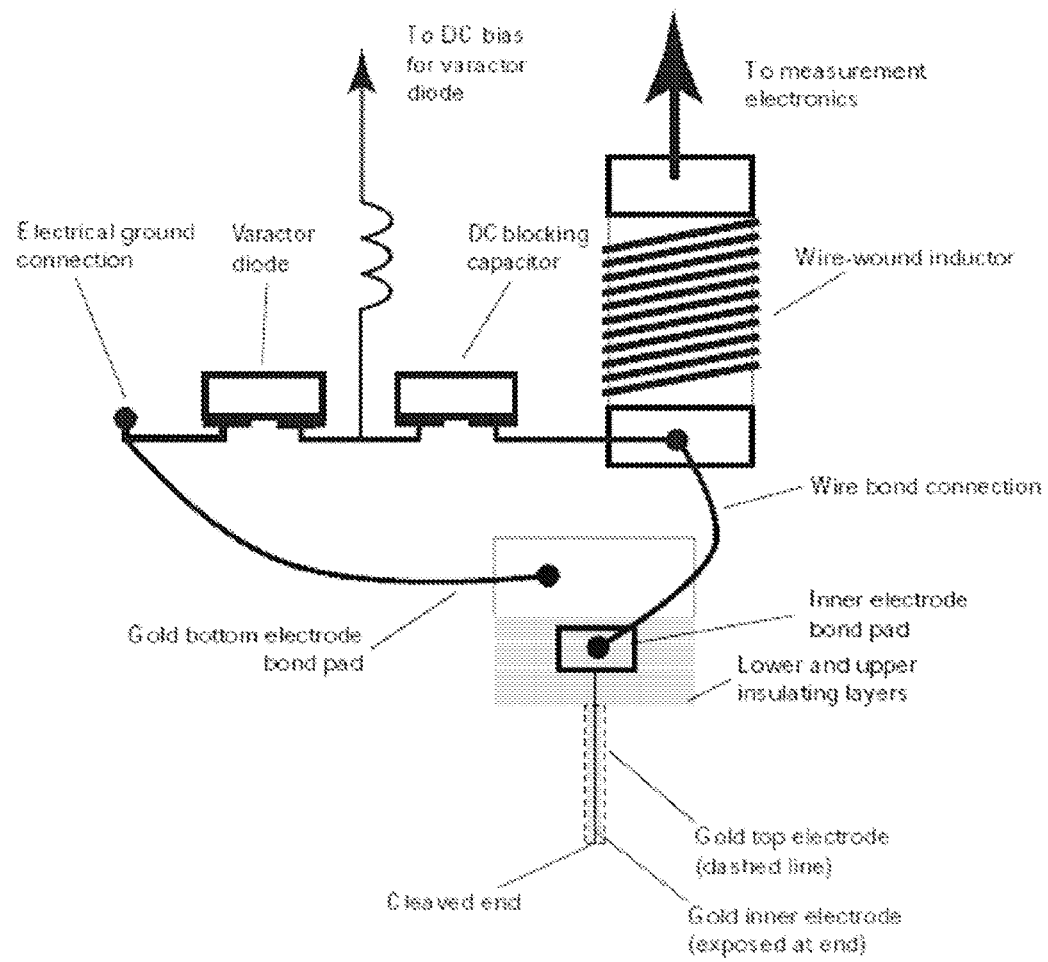
FIG. 13 is a larger scale schematic showing an example view of a structure of the form shown in FIG. 10, with a cleaved-end probe, here showing how electrical connections would be made to a discrete inductive component, to the signal ground, and to a varactor diode for impedance tuning, the latter optionally including a DC blocking capacitor and an RF blocking inductor at the appropriate locations of the circuit according to specific embodiments of the invention.

As a further example, FIG. 13 is a larger scale schematic showing an example view of a structure of the form shown in FIG. 10, with a cleaved-end probe, here showing how electrical connections would be made to a discrete inductive component, to the signal ground, and to a varactor diode for impedance tuning, the latter optionally including a DC blocking capacitor and an RF blocking inductor at the appropriate locations of the circuit according to specific embodiments of the invention.

Experimental Implementation

Figure 16:
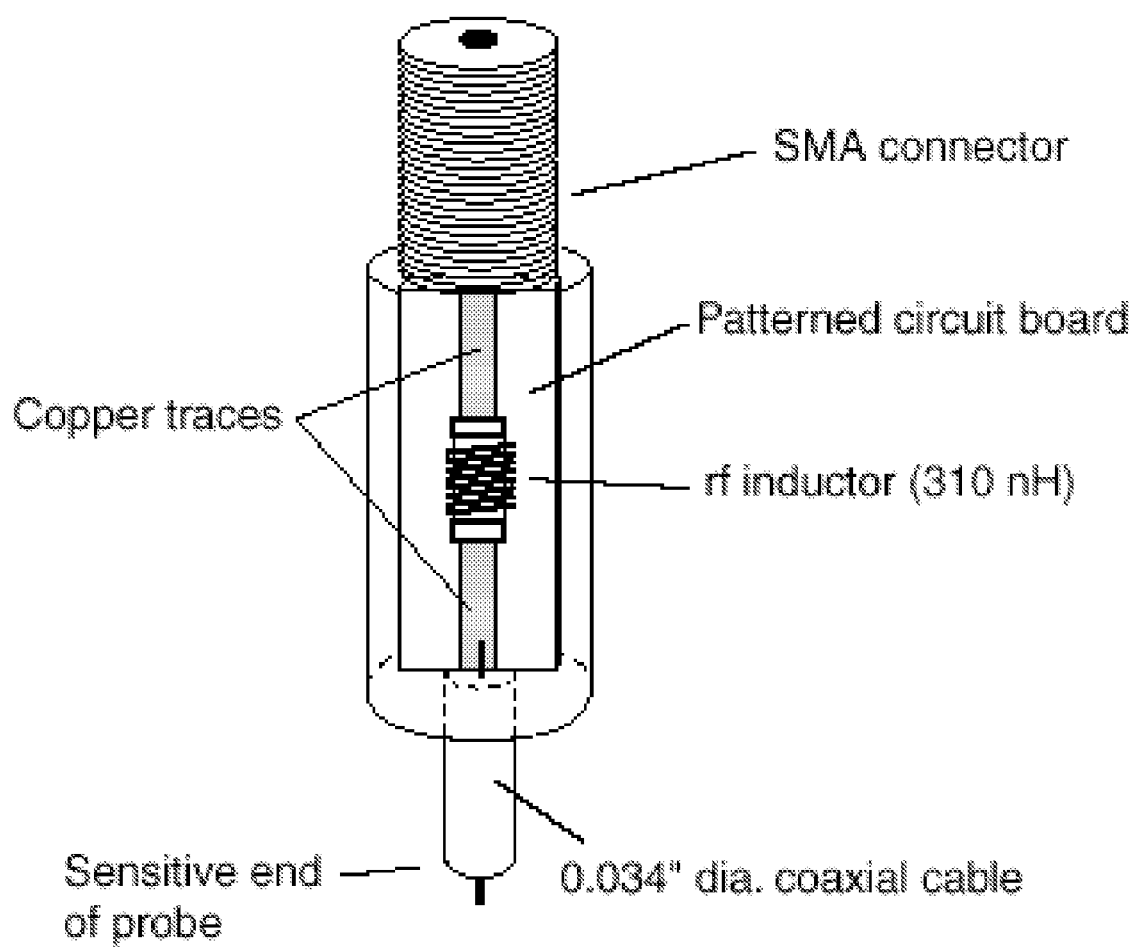
FIG. 16 is a schematic drawing showing an experimental prototype according to specific embodiments of the invention.

Prototype versions of coaxial probes according to specific embodiments of the invention were experimentally operated as proximal impedance sensors, in both fixed and scanned geometries, using metals, insulators, and electrolytic solutions as sample materials. FIG. 16 is a schematic drawing showing an experimental prototype according to specific embodiments of the invention. In this example, the detecting end of the probe is a 0.034 inch diameter coaxial cable, connected to a 310 nH radiofrequency inductor, the other end of which is connected to an sub-miniature radiofrequency connector to which a variety of electronics instruments can be connected.

Figure 17:
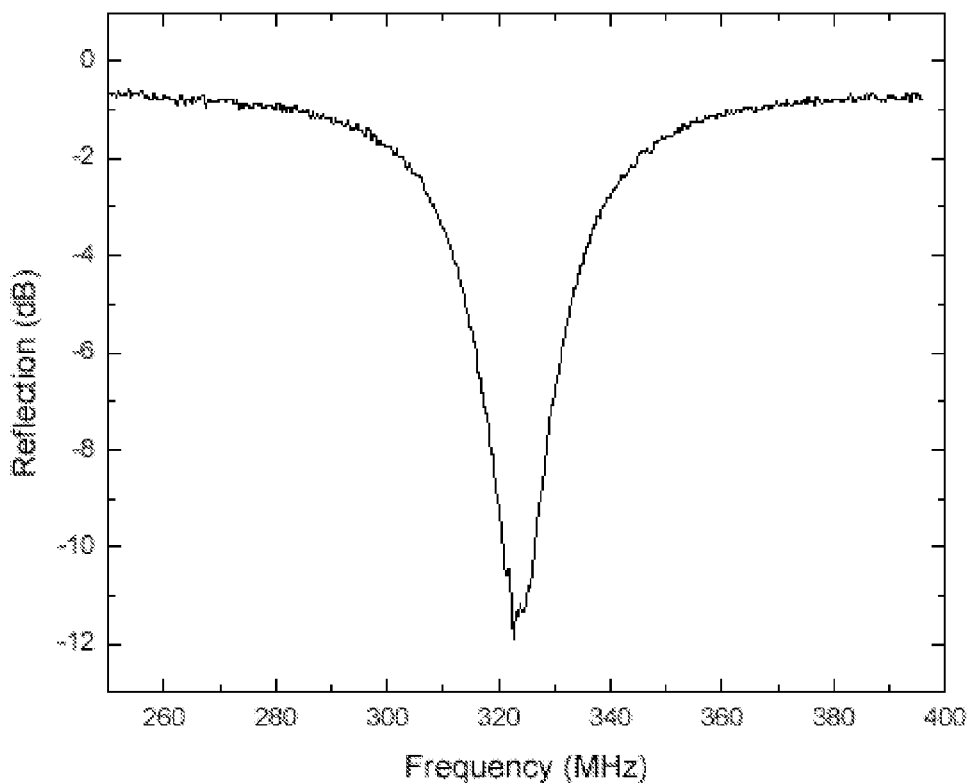
FIG. 17 illustrates an example of the experimental measured reflectance Abs[$S_1$] using a network analyzer for the prototype shown in FIG. 16 according to specific embodiments of the invention.

FIG. 17 illustrates an example of the experimental measured reflectance Abs[$S_1$] using a network analyzer for the prototype shown in FIG. 16 according to specific embodiments of the invention. This figure illustrates the measured reflection signal Abs[$S_1$] with no additional proximal impedance, showing a clear resonance frequency ($f_0$) at about 320 MHz with a bandwidth of about 15 MHz. In this example, the resonance dip at around 325 MHz corresponds to the frequency where the impedance match is ideal, yielding very low reflectance. Away from this frequency the impedance match is less perfect but still allows very sensitive and useful measurements according to specific embodiments of the invention.

Figure 18:
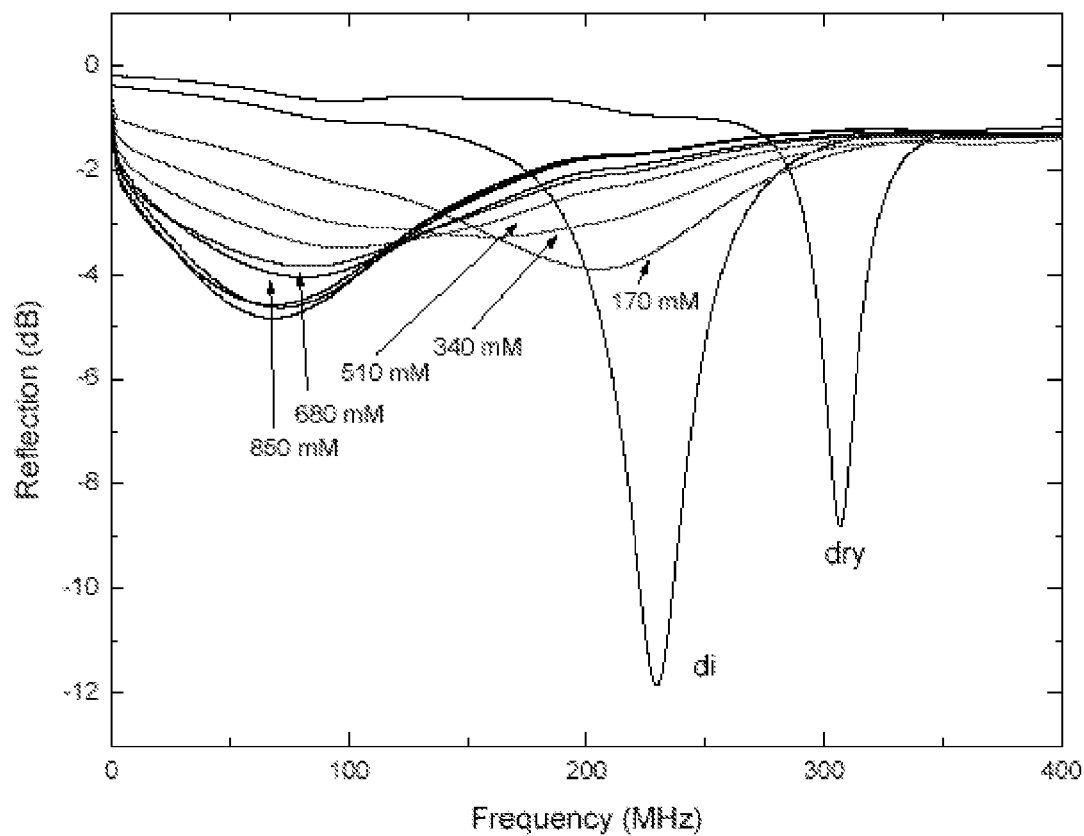
FIG. 18 illustrates an example of the experimental measured reflectance Abs[$S_1$] in air (dry), in distilled water (DI), and in varying concentrations of sodium chloride (NaCl) in water according to specific embodiments of the invention.

FIG. 18 illustrates an example of the experimental measured reflectance Abs[$S_1$] in air (dry), in distilled water (DI), and in varying concentrations of sodium chloride (NaCl) in water according to specific embodiments of the invention. In this figure, the detecting end of the probe is submerged in distilled water, in tap water, and then in distilled water with varying concentration of NaCl, from 170 mM up to 1.4 M, showing the range of salt concentrations that can be detected with this technique. In this example, both the resonance frequency and size of the resonance dip change as the salt concentration is increased. This is due to the increased conductance of the electrolyte. The resonant frequency and resonant height changes with the material and material composition because of changes in the real and imaginary parts of the impedance of the material. This changes the frequency at which the optimal matching is best approached, and the height of the peak changes due to how near optimum is approached.

Figure 19:
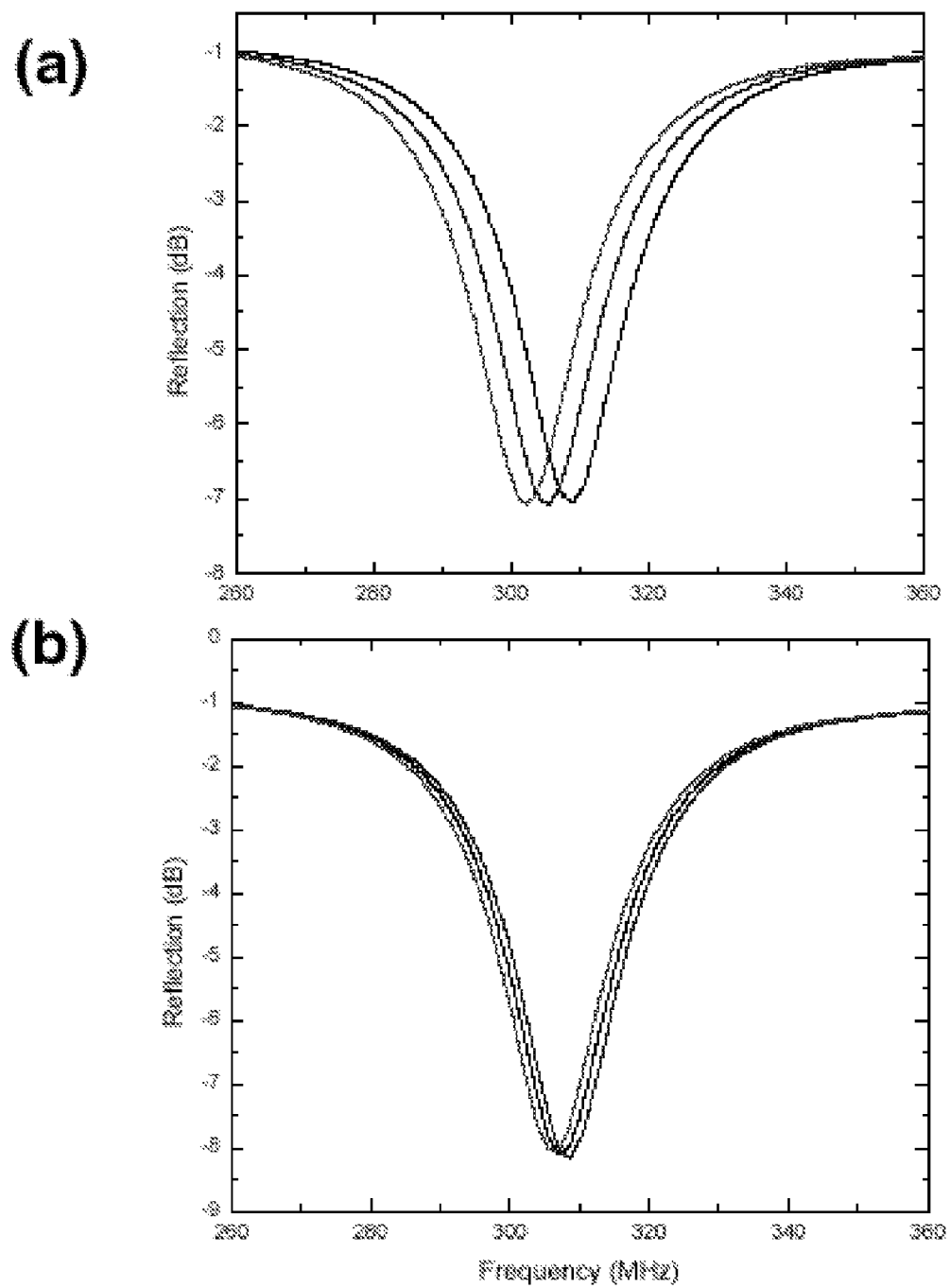
FIG. 19 illustrates an example of the experimental measured reflectance Abs[$S_1$] due (a) to the vertical approach of a copper plate, and (b) to the vertical approach of a glass plate according to specific embodiments of the invention.

FIG. 19 illustrates an example of the experimental measured reflectance Abs[$S_1$] due (a) to the vertical approach of a copper plate, and (b) to the vertical approach of a glass plate according to specific embodiments of the invention. In this example, measurements were made in air. The figures show the change in reflection Abs[$S_1$] as the probe approaches either a metal surface or a dielectric (glass surface), and shows that the position of minimum reflection shifts as the surface is brought closer to the probe. This shows the vertical displacement sensitivity achieved by this device.

In FIG. 19A, a plate of copper was brought up close to the end of the probe, oriented so that the probe axis was perpendicular to the plate, and resonances measured at a number of different heights between the probe end and the plate, shown here are for heights of 20, 70 and 140 μm. A clear shift in resonance frequency, due to the capacitive coupling between the metal plate and the probe inner conductor and outer shield, is apparent.

In FIG. 19A, a glass plate replaced the copper plate. The glass plate again is seen to shift the resonance frequency, due to the dielectric of the glass changing the coupling capacitance between the inner conductor and outer shield. Here the three curves are for probe-plate spacings of 20, 50 and 100 μm.

Figure 20:
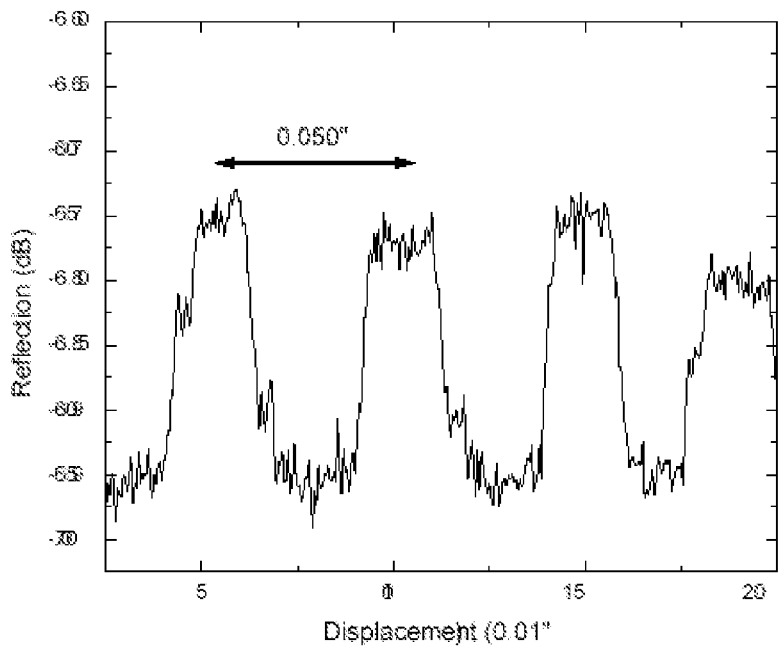
FIG. 20 illustrates an example of the experimental measured reflectance Abs[$S_1$] due to a scanning a patterned set of copper lines on a fiberglass backing (in this example, lines were 0.025 inches wide with 0.025 inch spacing) according to specific embodiments of the invention.

FIG. 20 illustrates an example of the experimental measured reflectance Abs[$S_1$] due to a scanning a patterned set of copper lines on a fiberglass backing (in this example, lines were 0.025 inches wide with 0.025 inch spacing) according to specific embodiments of the invention. The scan direction was perpendicular to the copper line direction, and the modulation in the reflected signal is clearly visible. The spatial resolution is set by the diameter of the coaxial probe (0.034 inch), but numerically corresponds to roughly $1/5^{th}$ the diameter. This measurement was made at constant frequency, chosen to correspond to the point of minimum reflection for this sample and choice of matching circuit.

Electrochemical Probe

According to further specific embodiments of the invention, a probe can be used as a specific, scanned electrochemical probe by detecting electrical properties at the probe end. In a similar application, the probe can be used to measure the ion channel activity in a biological cell, as well as measure the spatial distribution of ion channels in a biological setting.

4. Radiofrequency Probe for Microfluidic Cytometry

Overview

Some earlier approaches for electronic cell counting have been proposed by Renaud [1,2] and Sohn [3,4], and others. Sohn et al. used low-frequency capacitive cytometry, using audio frequency signals to drive a capacitance meter and detect biological cells directly from the change in effective capacitance in a micromachined microfluidic cytometer, where the detected signals were dominated apparently by the presence and quantity of DNA in the cell. The audio frequency-based cell cytometry was successful at direct cell detection, allowing counting and in some cases distinguishing different stages of division of mouse myeloma cells (SP2/0), and of rodent fibroblast cells (Rat-1). Some experiments also showed the ability to distinguish between cells with differing DNA content, but this approach does not directly allow distinguishing very similar cell types from one another. This group has also developed techniques to couple radiofrequency signals into microfluidic channels, allowing them to perform microwave spectroscopy on the contents of the channels, but this technique has not to our knowledge been applied to cytometry.

[1] S. Gawad, L. Schild, P. Renaud, "Micromachines impedance spectroscopy flow cytometer for cell analysis and particle sizing", *Lab on a Chip* 1, 76-82 (2001).
[2] S Gawad, K. Cheung, U. Seger, A. Bertsch, P. Renaud, "Dielectric spectroscopy in a micromachined flow cytometer", *Lab on a Chip* 4, 241-251 (2004).
[3] L. L. Sohn, O. A. Saleh, G. R. Facer, A. J. Beavis, R. S. Allan, D. A. Notterman, "Capacitance cytometry: Measuring biological cells one by one", *Proc. Natl. Acad. Sci.* 97, 10687-10690 (2000).
[4] G. R. Facer, D. A. Notterman, L. L. Sohn, "Dielectric spectroscopy for bioanalysis: From 40 Hz to 26.5 GHz in a microfabricated wave guide", *Appl. Phys. Lett.* 78, 996-998 (2001)

Renaud et al. have discussed using radiofrequency signals to detect and attempt to distinguish cells using radiofrequency coupled sensors, primarily in the low radiofrequency range (1 to 10 MHz). Their focus has been on detecting biological cells directly and their aim is to use variations in cell properties to distinguish cell strains from one another. Changes in the nature of the cellular membrane and cytoplasm (conductivity, permittivity, size, thickness, etc.) yield detectable variations in the detected signal, especially in the band of frequencies where the cellular electrical response changes from primarily conductive ion flow to primarily dielectric. Finite element simulations from this group indicate that measurements above and below this crossover frequency (closely related to the crossover frequency for dielectrophoretic force) may yield a distinguishable signal, when using a two-tone radiofrequency detection scheme tuned above and below the crossover.

Overview of Coulter counter and other Electronic Counting Methods

High throughput cell counting and analysis is an important biotechnological capability. Since the invention of the Coulter counter, electronic means to count and analyze biological cells have become an essential tool in hematology and oncology. In most implementations of the Coulter counter, the size and concentrations of cells are analyzed in real time, by monitoring the resistance changes in a narrow constriction.

The Coulter method of sizing and counting particles is based on measurable changes in electrical resistance generally produced by nonconductive particles suspended in an electrolyte. A small opening (aperture) between electrodes is the sensing zone through which suspended particles pass. In the sensing zone each particle displaces its own volume of electrolyte. Volume displaced is measured as a voltage pulse; the height of each pulse being proportional to the volume of the particle. In general, the quantity of suspension drawn through the aperture is precisely controlled to allow the system to count and size particles for an exact reproducible volume. In some systems, it is claimed that several thousand particles per second can be individually counted and sized. This method is independent of particle shape, color and density.

However, recent advancements in microfluidics offers a platform on which disposable, high resolution, high-throughput cell counters could be fabricated. While microfluidic platforms using the Coulter principle are presently under investigation, by a number of groups [26], achieving large electrical bandwidth in a microfluidic system presents challenges, due to the combination of high electrical impedance, presented by the small volume of ionic solution, with the inevitable stray capacitance of the sensing cabling. Thus, the standard Coulter principle may not be effectively adaptable to very small-scale or high speed devices.

Particle Counter According to Specific Embodiments of the invention

In further embodiments, the invention is involved with a radiofrequency probe useful for microfluidic cytometry in a microfluidic system. Such a probe and related systems and methods can be used, for example, in sensing and counting beads used to label biological cells or for sensing and counting cells directly. Direct applications are in cytometry, where the presence or type of cell or bead in a fluid stream is needed as an analytic tool.

As described above, radiofrequency probes according to various embodiments of the invention enable very high speed and sensitive detection of changes in the composition of fluids in contact with or near the probe's sensitive end. In further embodiments, this ability is applied to detecting heterogeneous changes in the fluid, due to either dielectric, metallic or magnetic beads in the fluid volume, or the presence of biological material, e.g. cells or viruses, in that same volume. The presence of such materials in the fluid volume, in the vicinity of the probe, causes changes in the electrical radiofrequency impedance detected by the probe. This change can be sensed by measuring the radiofrequency power reflected from the probe, or that transmitted through the probe, and monitoring changes in the amplitude, phase, and frequency dependence of these quantities. One particular advantage of this embodiment is the ability to detect labeled beads (dielectric, metallic or magnetic).

Thus, in further embodiments, the invention involves a method and/or system for high bandwidth, high sensitivity particle sensing and/or cell counting in a microfluidic system using a tuned radiofrequency probe. In this embodiment, the probe operates somewhat like a Coulter counter, but using a radiofrequency measurement rather than simple displacement resistance. By measuring the reflected radiofrequency power, this approach provides an unprecedented detection rate, with bandwidths in excess of 10 MHz (e.g., able to detect up to 10 million particles per second) in specific embodiments.

In an experimental setup, particle detection was performed in a continuous flow mode in a microfluidic channel, using 15 micron diameter polystyrene beads suspended in a sucrose-saline solution. 30 kHz counting rates and high-resolution bead time-of-flight data were demonstrated using an example system, comprising the fastest electronic particle detection in a microfluidic-chip system known by the inventors.

Using Detectably Distinguishable Beads

In this example implementation, the radiofrequency-based approach is developed for detection of labeling beads rather than cells, where the beads provide the molecular-level sensitivity of the sensor and further allows distinguishing multiple types of beads from one another (e.g., analogous to a color-sensitive scheme), allowing sorting of multiple labels simultaneously. The technique for distinguishing the beads from one another uses engineered beads to provide different dielectric/conducting signatures based on the bead dielectric and conductive properties, with beads coated with different detecting molecules or structures generally engineered to have different electrical properties. Thus, with such beads, various cell types or other biological discriminations can be made quickly, by detecting the electrical properties of those beads that react to or attach to the objects of interest and using the detected electrical properties of the beads to distinguish among varying biological or chemical substances or objects.

Example Counter Device and Fabrication

The present invention, according to specific embodiments, eliminates the effect of the stray capacitance through the use of a radiofrequency (rf) resonance detection technique [10, 12], where the stray capacitance is cancelled by a tank circuit inductance. This approach also achieves better rf impedance match to the sample volume, without sacrificing measurement bandwidth. Using this technique, prototypes according to specific embodiments of the invention have achieved approximately 100 times the throughput reported for other microfluidic electronic bead or cell detection schemes. Specific implementations of the invention have been demonstrated in a microfluidic flow mode that allows continuous measurement.

In specific embodiments, microfluidic devices with integrated rf electrodes are made using standard optical lithographic techniques. The microfluidic channels can be fabricated in a variety of suitable materials using a variety of microfabrication techniques. One example techniques uses molded polydimethyl siloxane [13] (PDMS) using a silicon mold [14]. As a further example, rf electrodes can be implemented using optically patterned, thermally evaporated gold/titanium lines (500 nm/10 nm thick) on glass chips, with microfluidic connections formed, for example, by drilling holes through the glass chips, and the chips are then aligned and bonded to the PDMS microchannel using a flip-chip bonder.

Figure 21:
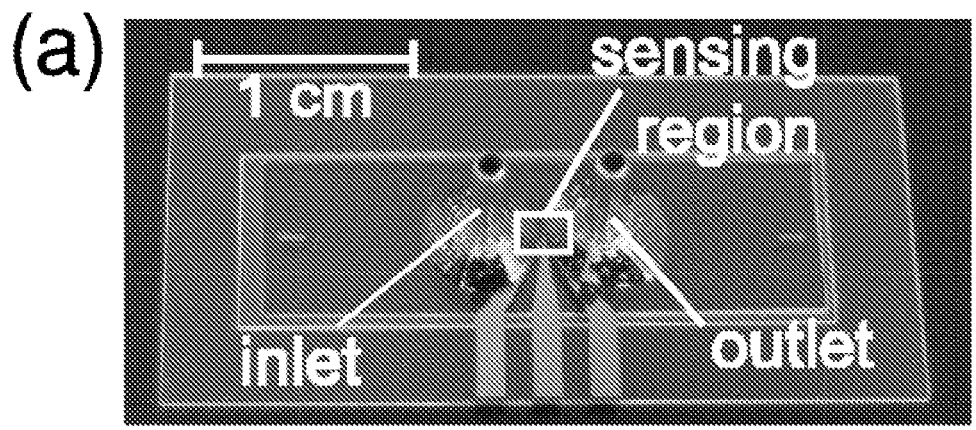
FIG. 21A shows a photograph of an example finished device, with fluidic connections according to specific embodiments of the invention. B is a schematic in an expanded form showing a 50 micron-wide fluidic channel with integrated coplanar electrodes according to specific embodiments of the invention.
Figure 21:
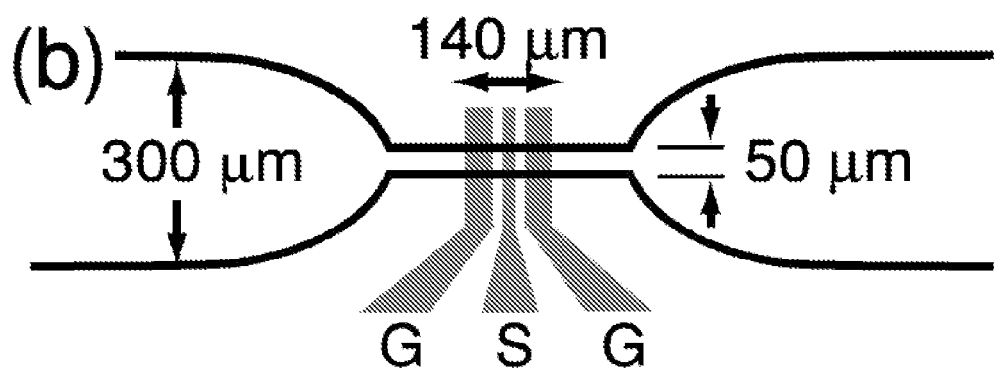

In an example system, the fluid connections are completed by fixing brass tubes to the chips with epoxy. A photograph of one example prototype device is shown in FIG. 21A. The microchannels are about 40 microns deep and either about 50 or 200 microns wide. The electrode geometry is a ground-signal-ground (G S G) coplanar stripline, which is a simplified implementation of the co-axial structure described elsewhere herein. In the microchannel the example signal electrode is about 20 microns wide, the example ground-signal spacing is about 20 microns, and the example ground electrodes are about 40 microns wide. The microwave stripline widens gradually from the region in the microchannel to the edge of the chip, where the strip width is made larger to accommodate soldering to a short length of stripline patterned on printed circuit board (PCB). The other end of the PCB stripline in this example is soldered to a sub-miniature (SMA) connector.

Electrical Characteristics of an Example Implementation

Figure 22:
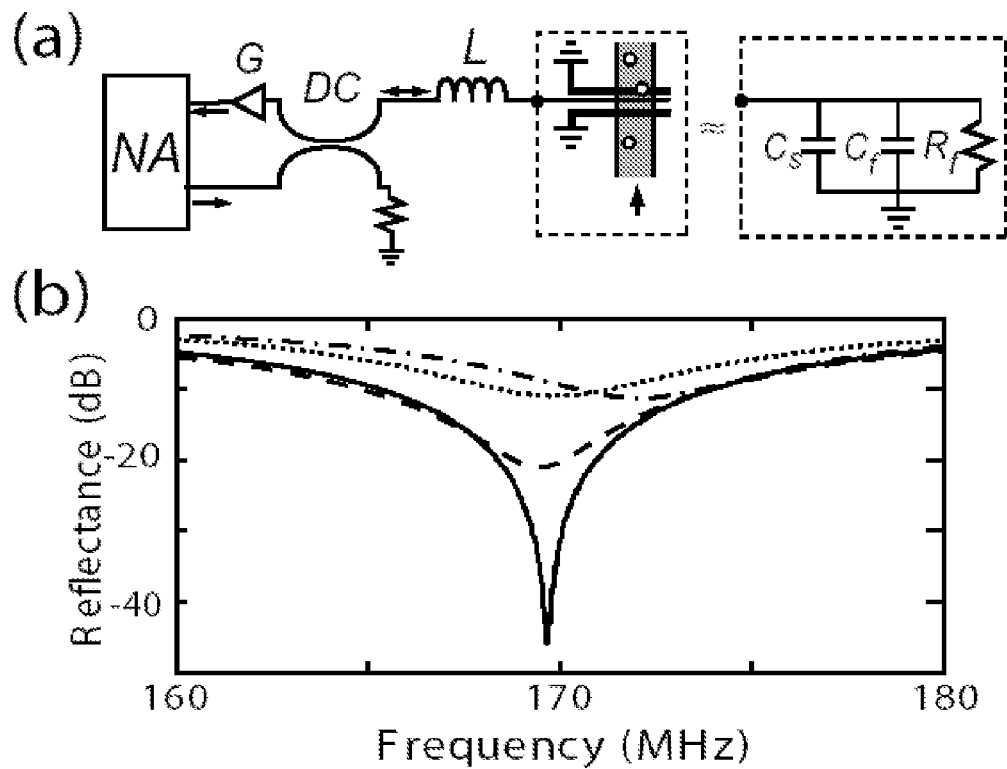
FIG. 22A is a circuit schematic showing a network analyzer NA, a low-noise amplifier G, and a directional coupler DC with the microchannel shown schematically in the left dashed box, and its lumped element representation shown in the right dashed box. B shows the measured reflectance Abs [$S_1$] with different solutions in the microchannel. Solid curve: Unit strength PBS with 0.168 g/mL sucrose; dashed curve: unit strength PBS; dotted line: deionized water; dot-dashed curve: dry microchannel according to specific embodiments of the invention.

The electrical impedance of the microwave stripline and fluid in the microchannel can be modeled by a parallel resistor-capacitor (RC) circuit, as shown in FIG. 22, which includes a stray capacitance $C_S$ and the resistance and capacitance of the fluid, $R_f$ and $C_f$. An inductor L is connected in series with this load, forming a tank circuit with the load capacitance $C_L = C_S + C_f$ resonant at the frequency $f_0 = \frac{1}{2\pi(LC)^{1/2}}$; at this frequency, the impedance of the circuit is purely resistive. With the appropriate inductance value, this resistive load (e.g., $R_f$) can be made equal to the 50 Ohm source impedance, and in addition achieves a measurement bandwidth $\Delta f$ of order 10-20% of the resonant frequency [11]. FIG. 22B shows the reflection $S_1(f)$ measured for a fixed inductance and different fluids in the microchannel, using an inductance L=470 nH. This yields a resonance frequency $f_0$=169 MHz when the microchannel is filled with unit concentration standard phosphate buffered saline [15] (PBS), to which we added 0.168 g/mL sucrose to achieve solution isodensity with the polystyrene beads (see below).

In various implementations, the value L is selected to complement the amplifier used (typical amplifiers work well over about one octave in frequency). Within the amplifier's range, a larger L is chosen for larger resistances, and a smaller L for smaller resistances. The stray capacitance is of course also involved in determining the frequency, so if the frequency is fixed and the stray capacitance known, then the optimum inductor is determined as indicated by the equations appearing above.

With an on-resonance reflectance $S_1 < -45$ dB, this circuit is very well impedance-matched and is thus sensitive to small changes in the load impedance, both resistive and capacitive. Removing the sucrose from the PBS (dashed curve) changes the reflectance dramatically, as does replacing the solution with DI water (dotted curve) or air (dot-dashed curve). The bandwidth $\Delta f$=25 MHz with the PBS-sucrose solution allows detection of signals with duration as short as 80 ns, which translates to a counting rate as high as 12 million particles (e.g. beads or biological cells) per second.

Experimental Counting Results

Following characterization of the rf properties of the sensor, we added a suspension of 15 micron diameter polystyrene beads to the solution [16]. The beads and solution were designed to be at isodensity to prevent settling. We then operated the device as a radiofrequency counter by monitoring the time-dependent reflection Abs[$S_1(t)$] as beads flowed through the microchannel. We measured Abs[$S_1$] at the resonance frequency of the device.

As the beads in the microchannel flow past the electrodes, they alter the effective impedance of the fluid mixture, modulating the probe reflectance $S_1$. On resonance, most of the power is absorbed by the fluid, making this a dark field measurement, with high contrast for small signals. Measurements were carried out with the circuit shown in FIG. 22A, using an injected power that corresponds to about 30 micro-W absorbed in the fluid, which causes a temperature change of at most 2.5 degrees C. in the ionic solution at a flow rate of 10 micro-L/hr. Reflected power was amplified by a room temperature radiofrequency amplifier.

Figure 23:
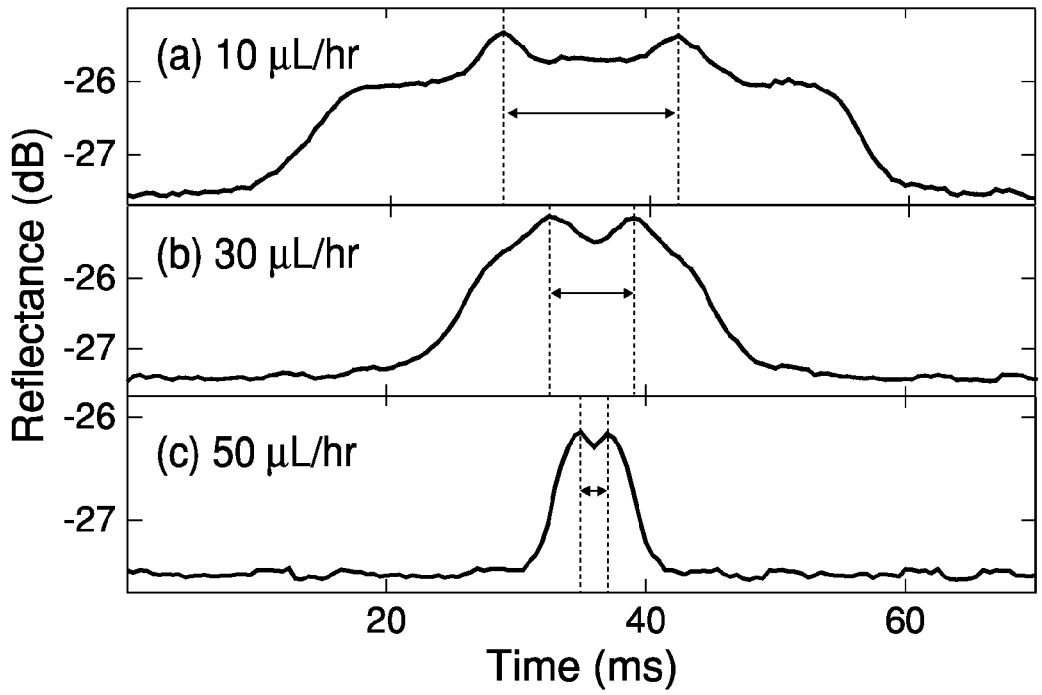
FIG. 23 illustrates time-of-flight data for 15 micron diameter beads flowing at (a) 10, (b) 30, and (c) 50 microL/hr where dashed vertical bars indicate peak-to-peak transit times, which correspond to a distance of 40 micrometers according to specific embodiments of the invention.

Flow through the microchannel was controlled using a syringe pump [17] while monitoring the reflectance signal. Signals were correlated by visual inspection and video monitoring through an optical microscope. Because of the high temporal resolution of the device, we were able to perform time-of-flight measurements for individual beads using a single set of electrodes. FIG. 23 shows time-domain data for 15 micron beads flowing through a 50 by 40 micron cross-section channel at 10, 30 and 50 micro-L/hr. The observed signals are large, with a 1-2 dB change in the signal as a bead passes through the electrode volume. Some variation is seen due to difference in the bead position in the channel, as reported by Gawad et al. [7].

The detailed shape of the curves in FIGS. 23A-C corresponds to onset as the bead crosses the first ground electrode (the initial rise), two peaks as the bead crosses the region between the signal and two ground electrodes (with the dip occurring roughly nearest the ground electrode), and decaying as the bead passes the second ground electrode. The regions between the signal and two ground electrodes are those with the highest electrical field, so the two peaks in the response correspond to when the beads are passing through these regions. Hence in this embodiment the peak-to-peak traversal time corresponds to the midpoint-to-midpoint distance of 40 microns, from which can be determined the bead velocity. The beads in FIGS. 23A, B and C give peak-to-peak transit times of 14 ms, 6.3 ms, and 2.4 ms respectively, which correspond to bead velocities of 2.9 mm's, 6.4 mm's, and 17 mm/s. A flow rate of 10 microL/hr in this channel corresponds to a theoretical maximum channel velocity of 2.9 mm's and a transit time of 14 ms [18]. Similarly, we expect transit times and velocities of 4.6 ms (8.7 mm/s) and 2.8 ms (15 mm's) for the 30 microL/hr and 50 microL/hr flow rates respectively. The measured bead velocity varies from bead to bead depending on the bead location in the channel, and is typically smaller but close to that expected.

Figure 24:
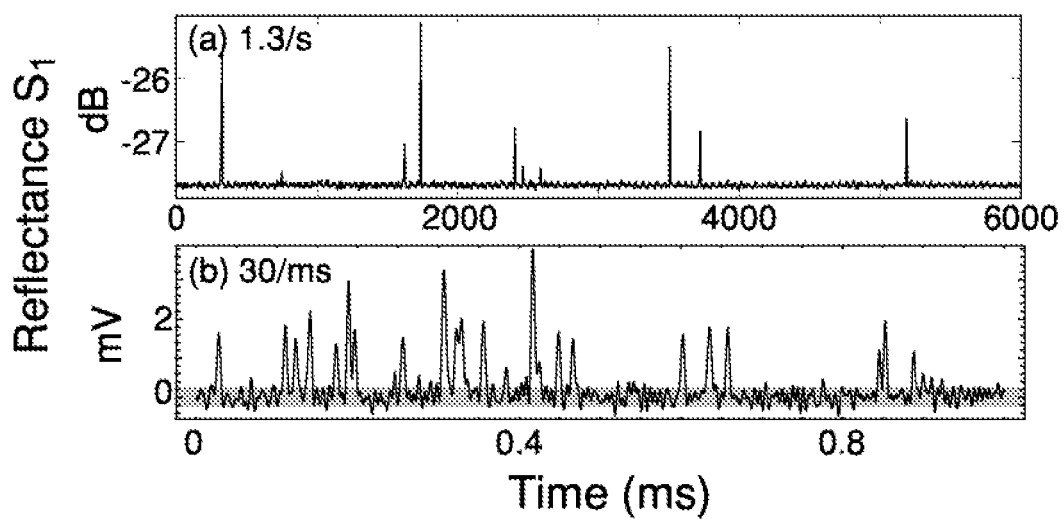
FIG. 24 illustrates measured absolute reflectance Abs[$S_1$] measured with 15 micrometer diameter beads (a) flowing at 1.3 beads/second and (b) flowing at 30,000 beads/second. Note the horizontal and vertical scales are different. The gray bar indicates the noise level for (b). Data in (b) is at output of mixer-amplifier combination, with a combined voltage gain of 32.

We then performed measurements at longer time scales to extract bead count rates as a function of flow rate. FIG. 24A shows the time-dependent reflection for 15 micron beads at a concentration of 46 beads/microL flowing at 100 microL/hr through a 50 by 40 micron$^2$ channel, corresponding to a maximum flow velocity of 30 mm/s and a transit time of about 1.3 ms. The peaks in $S_1$ are again very distinct, with variations in peak height corresponding to variations in bead position in the channel. The flow rate corresponds to 1.3 beads/second, and is close to the measured rate of 1.4/second. We then greatly increased the flow rate, and measured at a calculated rate of 30,000 beads/second. For this measurement we used a homodyne mixer to demodulate the rf signal, which was then amplified by a 1 MHz bandwidth amplifier, and flowed the beads through a 200 by 40 micron$^2$ channel. After digital filtering the measurement bandwidth was 175 kHz. FIG. 24B shows a typical data trace captured with this arrangement. The bead count rate of 25/ms is close to the calculated value of 30/ms. This rate is roughly 100 times that reported for other electronic detection schemes [3], and is comparable to that of commercial fluorescence activated cell sorters (FACS) [19].

The limit for bead detection ultimately will be set by the signal to noise ratio S/N, which is reduced as the measurement bandwidth is increased to follow the count rate. Higher signal powers yield a better (higher) signal-to-noise ratio S/N, as does the use of low-noise amplifiers. The width of the gray box in FIG. 24B corresponds to a noise level of 26 nV/Hz$^{1/2}$ referenced to the amplifier input, and with the digital bandwidth of 175 kHz yields a S/N ratio of about 4; smaller values will yield poor counting statistics. The noise level for the setup is dominated by the rf electronics.

In conclusion, we have demonstrated the use of a tuned rf circuit as a microchannel particle counter. This implementation has an intrinsic bandwidth in excess of 10 MHz, allowing count rates approaching millions of beads, or cells, per second. We have shown measurement of 15 m polystyrene beads at different rates, demonstrating both time-of-flight and high flow rate measurements, up to 30 kHz. This technique, with its intrinsically high throughput and sensitivity, could play a significant role in the future development of electrically-based microfluidic systems for disposable cellular analysis.

5. Diagnostic Uses

As described above, following identification and validation of a sensor for a particular substance, including biological molecules such as sugars, proteins, fats, particular cell types or cellular characteristics, or any substance of interest according to the invention, in specific embodiments such detectors are used in clinical or research settings, such as to predictively categorize subjects into disease-relevant classes, to monitor subjects to detect a substance of interest, etc. Detectors according to the methods the invention can be utilized for a variety of purposes by researchers, physicians, healthcare workers, hospitals, laboratories, patients, companies and other institutions. For example, the detectors can be applied to: diagnose disease; assess severity of disease; predict future occurrence of disease; predict future complications of disease; determine disease prognosis; evaluate the patient's risk; assess response to current drug therapy; assess response to current non-pharmacologic therapy; determine the most appropriate medication or treatment for the patient; and determine most appropriate additional diagnostic testing for the patient, among other clinically and epidemiologically relevant applications. Essentially any disease, condition, or status for which a substance or difference can be detected in an interstitial fluid can be evaluated, e.g., diagnosed, monitored, etc. using the diagnostic methods of the invention, see, e.g. Table 1. Essentially any disease, condition, or status for which a substance can be delivered to effect treatment to interstitial fluid can be treated, using the diagnostic methods of the invention, see, e.g. Table 1.

In addition to assessing health status at an individual level, the methods and diagnostic sensors of the present invention are suitable for evaluating subjects at a "population level," e.g., for epidemiological studies, or for population screening for a condition or disease.

Kits

A detector according to specific embodiments of the present invention is optionally provided to a user as a kit. Typically, a kit of the invention contains one or more sensors constructed according to the methods described herein. Most often, the kit contains a diagnostic sensor packaged in a suitable container. The kit optionally further comprises an instruction set or user manual detailing preferred methods of using the kit components for sensing a substance of interest.

When used according to the instructions, the kit enables the user to identify disease or condition specific substances or cells using patient tissues, including, but not limited to whole blood, separated blood, interstitial fluids, suspensions of cells, etc. The kit can also allow the user to access a central database server that receives and provides information to the user. Additionally, or alternatively, the kit allows the user, e.g., a health care practitioner, clinical laboratory, or researcher, to determine the probability that an individual belongs to a clinically relevant class of subjects (diagnostic or otherwise).

Embodiment in a Programmed Information Appliance

The invention may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

Other Integrated System Components

A system according to specific embodiments of the invention can have a number of components depending on the particular detecting application. Systems can include mechanical positioning supports and controls, a fluid reservoir, fluidic channels, micropumps and valves and can also include components for connecting to a computer and/or information processing system, either through a physical adaptor or wireless connection.

Integrated systems for the collection and analysis of detection results, including detection or expression profiles, molecular signatures, as well as for the compilation, storage and access of the databases of the invention, typically include a digital computer with software including an instruction set for various analysis, and, optionally, one or more of high-throughput sample control software, image analysis software, data interpretation software, robotic or fluidic controls for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises an electronic signal generator and detection scanner for probing electrical properties of samples.

Readily available computational hardware resources using standard operating systems can be employed and modified according to the teachings provided herein, e.g., a PC (Intel x86 or Pentium chip-compatible DOS™, WINDOWS™, LINUX™, or Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the described data and/or electrical analysis can be constructed by one of skill using a standard programming language such as Visual Basic, Fortran, Basic, Java, or the like. Such software can also be constructed utilizing a variety of statistical programming languages, toolkits, or libraries.

FIG. 25 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention is also included in the computer systems of the invention.

OTHER EMBODIMENTS

Although the present invention has been described in terms of various specific embodiments, it is not intended that the invention be limited to these embodiments. Modification within the spirit of the invention will be apparent to those skilled in the art. It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed is:

1. A device capable of measuring impedance variances in a small region comprising:
a probe electrode separated by one or more non-conducting regions from one or more shield electrodes;
a detecting end of said probe electrode that can be placed in close proximity to said small region;
an inductor L operatively connected to said probe electrode and to a transmission conductor connecting to measurement electronics;
a signal generator for generating a radiofrequency signal; and
impedance measurement electronics able to measure a reflected signal and thereby determine impedance variances at said functional end.

2. The device of claim 1 further comprising:
a varactor diode that acts as a controllable capacitance Cv operatively connected to said probe electrode, said inductor and to a transmission conductor connecting to measurement electronics.

3. The device of claim 2 further wherein:
a stray capacitance between said probe and said one or more shield electrodes C resonates with said inductor L and said varactor diode forming a tunable LC resonant circuit with an approximate resonance frequency $f^0 = (1/2)(1/L(C+C_V))^{1/2}$ wherein said resonance frequency can be tuned by adjusting the effective capacitance Cv.

4. The device of claim 2 further comprising:
a second inductor L2 operatively connected to said varactor and said inductor L and a DC source that allows separate DC tuning of the varactor diode (indicated as a variable capacitor $C_V$) and RF reflectance;
wherein inductor L2 allows a DC bias circuit to be isolated from an RF part of the device.

5. The device of claim 1 further wherein:
said probe electrode, said detecting end, and said inductor L are configured in a planar geometry.

6. The device of claim 2 further wherein:
said probe electrode, said detecting end, said inductor L, and said varactor are configured in a planar geometry.

7. The device of claim 1 further wherein:
a stray capacitance between said probe and said one or more shield electrodes C resonates with said inductor L, forming an LC resonant circuit with an approximate resonance frequency $f_0 = (1/2\pi)(1/LC)^{1/2}$.

8. The device of claim 1 further wherein:
said inductor L includes a small series resistance r, thereby generating a measured reflectance loss with a peak centered at the resonance frequency $f_0$ such that if a sample is placed near the detecting end of the probe, so that it couples to the electromagnetic fields emanating from the probe end, the effective capacitance and resistance of the sample impedance changes the reflectance loss.

9. The device of claim 8 further wherein:
a capacitive part of the sample impedance changes the resonance frequency $f_0$; and
a resistive part of the sample impedance changes the magnitude of the reflection loss.

10. A method for measuring impedance variations in a small volume comprising:
placing a microfabricated probe with a detecting end in proximity to said volume; and
using a tank circuit to couple said microfabricated probe to radiofrequency circuitry; and impedance measurement electronics able to measure a reflected signal and thereby determine impedance variances at said functional end of said microfabricated probe.

11. The method of claim 10 further wherein:
said tank circuit comprises a lumped inductor in parallel with a stray and optionally a lumped capacitance.

12. The method of claim 10 further wherein:
said probe comprises a sharp tip analogous to a scanning tunneling microscope tip, with a metal shield surrounding it.

13. The method of claim 10 further wherein:
said probe comprises a planar geometry with a ground-signal-ground arrangement.

14. The method of claim 10 further wherein:
said tank circuit comprises:
a variable capacitor diode ("varactor") that can function as an electronically controlled tuning element to improve impedance matching.

15. The method of claim 14 further wherein:
said varactor is co-fabricated on a same substrate as said microfabricated probe.

16. The method of claim 10 further wherein:
said probe and related radiofrequency electronics senses changes in absolute and/or real and/or imaginary part of impedance presented by a sample;
said sample comprises one or more selected from the group comprising:
a solid object, possibly with mechanical degrees of freedom;
a fluid, possibly with ions or other molecules dissolved in it; and
a surface on which objects or molecules attach themselves and are sensed or otherwise measured.

17. The method of claim 10 further wherein:
a distance between said probe and a ground connection is adjustable, thereby adjusting the particle size sensitivity.

18. The device of claim 1 further wherein:
said impedance measurement electronics and said probe are constructed to detect particles in a fluid.

19. The device of claim 18 further wherein:
said particles can include biological cells or labeling beads, either dielectric or metal, or other particles contained in the fluid with different electrical properties from the fluid (including inhomogeneous mixtures of two or more fluids).

20. The device of claim 18 further wherein:

said probe can be used to sense materials or objects attached to the particles.

21. The device of claim 18 further wherein:

said probe can be used for one or more of:

measuring flow rates;
measuring concentrations of particles;
distinguishing particles in a mixed fluid stream; and
measuring diffusion rates of particles.

* * * * *